(12) United States Patent
Steeneck et al.

(10) Patent No.: US 11,376,241 B2
(45) Date of Patent: *Jul. 5, 2022

(54) ARYL HYDROCARBON RECEPTOR (AHR) MODULATOR COMPOUNDS

(71) Applicant: PHENEX PHARMACEUTICALS AG, Ludwigshafen (DE)

(72) Inventors: Christoph Steeneck, Heidelberg (DE); Ulrich Deuschle, Speyer (DE); Michael Albers, Mannheim (DE); Thomas Hoffmann, Speyer (DE)

(73) Assignee: PHENEX PHARMACEUTICALS AG, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/479,847

(22) PCT Filed: Feb. 1, 2018

(86) PCT No.: PCT/EP2018/052538
§ 371 (c)(1),
(2) Date: Jul. 22, 2019

(87) PCT Pub. No.: WO2018/141855
PCT Pub. Date: Aug. 9, 2018

(65) Prior Publication Data
US 2021/0260045 A1 Aug. 26, 2021

(30) Foreign Application Priority Data
Feb. 1, 2017 (EP) .................... 17000157

(51) Int. Cl.
*A61K 31/437* (2006.01)
*A61K 45/06* (2006.01)
*C07D 471/04* (2006.01)
(52) U.S. Cl.
CPC ............ *A61K 31/437* (2013.01); *A61K 45/06* (2013.01); *C07D 471/04* (2013.01)
(58) Field of Classification Search
CPC ..... A61K 31/437; A61K 45/06; C07D 471/04
USPC ....................................................... 514/300
See application file for complete search history.

(56) References Cited

U.S. PATENT DOCUMENTS

| 8,901,118 B2 | 12/2014 | Zhang et al. |
| 9,102,672 B2 | 8/2015 | Hadida-Ruah et al. |
| 9,676,748 B2 | 6/2017 | Wu et al. |
| 10,981,908 B2 * | 4/2021 | Steeneck .............. A61K 31/437 |
| 2004/0180946 A1 | 9/2004 | Sircar et al. |
| 2012/0295904 A1 | 11/2012 | Zhi et al. |
| 2013/0338201 A1 | 12/2013 | Song |
| 2016/0175278 A1 | 6/2016 | Sherr et al. |
| 2020/0031805 A1 | 1/2020 | Deuschle et al. |

FOREIGN PATENT DOCUMENTS

| WO | 92/02500 A1 | 2/1992 |
| WO | 98/22457 A1 | 5/1998 |
| WO | 2005/005414 A2 | 1/2005 |
| WO | 2007/057329 A1 | 5/2007 |
| WO | 2011/097079 A1 | 8/2011 |
| WO | 2011/117264 A1 | 9/2011 |
| WO | 2011/133637 A2 | 10/2011 |
| WO | 2012/123745 A1 | 9/2012 |
| WO | 2014/060328 A1 | 4/2014 |
| WO | 2014/100620 A2 | 6/2014 |
| WO | 2018/141855 A1 | 8/2018 |
| WO | 2018/141857 A1 | 8/2018 |
| WO | 2018/153893 A1 | 8/2018 |

OTHER PUBLICATIONS

Sebastien Naud et al Structure-Based Design of Orally Bioavailable 1-H-Pyrrolo[3,2-c]pyridine inhibitors of Mitotic Kinase Monopolar Spindle 1(MPS1) (Year: 2013).*
Kerkvliet, "AHR-mediated immunomodulation: The role of altered gene transcription," *Biochemical Pharmacology* 77: 746-760, 2009.
Monteleone et al., "The aryl hydrocarbon receptor in inflammatory bowel disease: linking the environment to disease pathogenesis," *Curr. Opin. Gastroenterol.* 28: 310-313, 2012.
Vezina et al., "AHR signaling in prostate growth, morphogenesis, and disease," *Biochemical Pharmacology* 77: 566-576, 2009.
Official Action from Chile Ministerio de Economia dated Jul. 13, 2020, for Application No. 201902108 filed Feb. 1, 2018, 12 pages.
Official Action from Intellectual Property India dated Sep. 11, 2020, for Application No. 201917029343, 5 pages.
Official Action from Japan Patent Office dated Sep. 15, 2020, for Application No. 2019-561370, 3 pages (translation).
Official Action from Intellectual Property India dated Mar. 17, 2020, for Application No. 201917029340, 6 pages.
Bessede et al., "Aryl hydrocarbon receptor control of a disease tolerance defence pathway," *Nature* 511: 184-190, 2014 (19 pages).
Foster, "Deuterium isotope effects in studies of drug metabolism," *Trends in Pharmacological Sciences* 5: 524-527, 1984 (5 pages).
Hanan et al., "Discovery of Selective and Noncovalent Diaminopyrimidine-Based Inhibitors of Epidermal Growth Factor Receptor Containing the T790M Resistance Mutation," *J. Med. Chem.* 57: 10176-10191, 2014.

(Continued)

*Primary Examiner* — Nizal S Chandrakumar
(74) *Attorney, Agent, or Firm* — Seed IP Law Group LLP

(57) ABSTRACT

The present invention relates to compounds which can act as aryl hydrocarbon receptor (AhR) modulators and, in particular, as AhR antagonists. The invention further relates to the use of the compounds for the treatment and/or prophylaxis of diseases and/or conditions through binding of said aryl hydrocarbon receptor by said compounds.

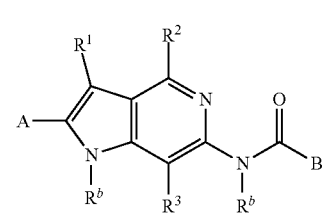

(I)

14 Claims, No Drawings

(56) References Cited

OTHER PUBLICATIONS

Koliopanos et al., "Increased arylhydrocarbon receptor expression offers a potential therapeutic target for pancreatic cancer," *Oncogene* 21: 6059-6070, 2002.

Li et al., "Expression of aryl hydrocarbon receptor in relation to p53 status and clinicopathological parameters in breast cancer," *Int. J. Clin. Exp. Pathol.* 7(11): 7931-7937, 2014.

Li et al., "Leadopt: An automatic tool for structure-based lead optimization, and its application in structural optimizations of VEGFR2 and SYK inhibitors," *European Journal of Medicinal Chemistry* 93: 523-538, 2015.

Murray et al., "AH Receptor Ligands in Cancer: Friend and Foe," *Nat. Rev. Cancer* 14(12): 801-814, 2014.

Naud et al., "Structure-Based Design of Orally Bioavailable 1H-Pyrrolo[3,2-c]pyridine Inhibitors of Mitotic Kinase Monopolar Spindle 1 (MPS1)," *J. Med. Chem.* 56: 10045-10065, 2013.

Richmond et al., "The Aryl Hydrocarbon Receptor Is Constitutively Active in Advanced Prostate Cancer Cells," *PLOS One* 9(4): e95058, 2014 (11 pages).

Romani et al., "Microbiota control of a tryptophan-AhR pathway in disease tolerance to fungi," *Eur. J. Immunol.* 44: 3192-3200, 2014.

Safe et al., "Role of the Aryl Hydrocarbon Receptor in Carcinogenesis and Potential as a Drug Target," *Toxicological Sciences* 135(1): 1-16, 2013.

Zelante et al., "Tryptophan Catabolites from Microbiota Engage Aryl Hydrocarbon Receptor and Balance Mucosal Reactivity via Interleukin-22," *Immunity* 39: 372-385, 2013.

Official Action from European Patent Office re extended European search report, dated Mar. 22, 2017, for Patent Application No. 17000157.2, 10 pages.

Official Action from European Patent Office re extended European search report, dated Mar. 23, 2017, for Patent Application No. 17000158.0, 4 pages.

Official Action from European Patent Office re extended European search report, dated Mar. 30, 2017, for Patent Application No. 17000276.0, 5 pages.

International Search Report, dated Mar. 12, 2018, for International Application No. PCT/EP2018/052542, 4 pages.

International Search Report, dated Mar. 29, 2018, for International Application No. PCT/EP2018/052538, 5 pages.

International Search Report, dated May 3, 2018, for International Application No. PCT/EP2018/054234, 5 pages.

* cited by examiner

ARYL HYDROCARBON RECEPTOR (AHR) MODULATOR COMPOUNDS

The present invention relates to compounds which can act as aryl hydrocarbon receptor (AhR) modulators and, in particular, as AhR antagonists. The invention further relates to the use of the compounds for the treatment and/or prophylaxis of diseases and/or conditions through binding of said aryl hydrocarbon receptor by said compounds.

The aryl hydrocarbon receptor (AhR) is a ligand-modulated transcription factor, belonging to the basic helix-loop-helix PAS (Per-Arnt-Sim homology domain) family, that is expressed in most tissues in mice and humans and known to mediate many of the toxicities of 2,3,7,8-Tetrachlorodibenzo-p-dioxin (TCDD) in mice. The AhR protein is localized in the cytoplasm of eukaryotic cells in complexes with HSP90 and other proteins. Binding of agonistic ligands, such as TCDD, leads to dissociation of AhR from the HSP90 containing complex, transport to the nucleus and association with its heterodimeric partner ARNT. This heterodimeric complex can bind to AhR response elements located in promoter regions of genes such as CYP1A1, CYP1B1, ALDH3A1, NQO1, UGT1A1 etc. and induces the transcription of such genes in case of very potent and efficacious AhR agonists, such as TCDD.

By regulating the expression of genes involved in xenobiotic transformation (e.g. CYP1A1), the AhR plays a significant role in the detoxification of xenobiotic substances in liver and intestine, which are prominent locations of AhR expression. This activity might be underlying some of the described chemoprevention and tumor suppression effects exerted by AhR. On the other hand, CYP1A1 is known to metabolize some pro-cancerogens, such as benzo(a)pyrene into DNA reactive intermediates leading to mutagenesis and tumor formation (Murray et al. Nat Rev Cancer. 2014 December; 14(12):801-14; Safe et al Toxicol Sci. 2013 September; 135(1):1-16).

In mouse cancer models, knock-down of AhR typically resulted in decreased proliferation and/or invasion and migration of cancer cell lines and overexpression of constitutive active AhR results in vivo in enhanced stomach and liver cancers (Safe et al Toxicol Sci. 2013 September; 135(1):1-16).

The AhR is relatively strongly expressed in intestinal epithelial tissues, lung epithelium and skin. In these tissues the AhR expression is particularly high in cells of lymphoid origin such as T-cells, Dendritic Cells, Langerhans Cells, Macrophages, Mast cells etc. One possible function in these compartments is to integrate signals from the commensal microbiomes in the intestine, the lung and the skin, which are known to produce diverse mixtures of indolic AhR modulators that are thought to balance the responses of the immune system towards the microbiome (Bessede et al., Nature. 2014 Jul. 10; 511(7508):184-90, Zelante et al. Immunity. 2013 Aug. 22; 39(2):372-85, Romani et al., Eur J Immunol. 2014 November; 44(11):3192-200).

The expression of AhR has been found to be constitutive active in advanced human prostate cancer (Richmond et al., 2014, PLoS ONE 9(4): e95058), overexpressed in breast cancer (Li et al., Int J Clin Exp Pathol. 2014 Oct. 15; 7(11):7931) and pancreas cancer (Koliopanos et al., Oncogene. 2002 Sep. 5; 21(39):6059-70). Modulation of the AhR pathway activity by small molecule modulators might be beneficial for some of these devastating diseases with very limited treatment options.

In a recently published Patent Application US 2016/01752278 by the Trustees of Boston University, novel small molecule agents characterized as AhR modulators are being claimed for inhibiting cancer cell proliferation and tumor cell invasion and metastasis.

AhR modulators and in particular modulators with primarily antagonistic activities might be useful as medicaments for the treatment of solid tumors (e.g., pancreatic cancer, prostate cancer, breast cancer, colon cancer).

The problem underlying the present invention is to provide compounds which have a AhR-antagonistic activity and can be used in the treatment and/or prophylaxis of AhR-mediated diseases.

Said problem has been solved by a compound according to the following Formula (I), an enantiomer, diastereomer, tautomer, solvate, prodrug or pharmaceutical acceptable salt thereof

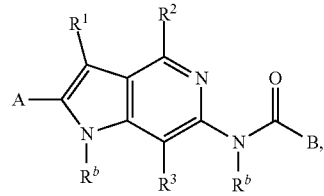

wherein

A and B are independently selected from 6- to 10-membered mono- or bicyclic aryl and 5- to 10-membered mono- or bicyclic heteroaryl containing 1 to 4 heteroatoms independently selected from N, O and S, wherein aryl and heteroaryl are unsubstituted or substituted with 1 to 7 substituents independently selected from the group consisting of halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$, NWS(O)$_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, OH, CN and oxo; or wherein two substituents on the aryl or heteroaryl group together with the atoms they are attached to may form a 5 to 7-membered saturated or partially unsaturated carbocyclic ring or heterocyclic ring containing 1 to 3 heteroatoms independently selected from O, N and S, wherein the carbocyclic or heterocyclic ring is unsubstituted or substituted with 1 to 5 substituents independently selected from the group consisting of halogen, $C_{1-6}$-alkyl and halo-$C_{1-6}$-alkyl;

$R^1$, $R^2$, $R^3$ are each independently selected from hydrogen, halogen, $C_{1-3}$-alkyl, halo-$C_{1-3}$-alkyl, OH, O—$C_{1-3}$-alkyl, and CN;

$R^a$ is hydrogen or $C_{1-6}$-alkyl, and $R^b$ is hydrogen or $C_{1-6}$-alkyl.

In another embodiment in combination with any of the above or below embodiments, $R^b$ in the compound according to Formula (I) is hydrogen.

In another embodiment in combination with any of the above or below embodiments, A in the compound according to Formula (I) is substituted with 1 to 5 substituents independently selected from halogen, $C_{1-6}$-alkyl, $C_{1-6}$-haloalkyl, CN, SO$_2$CH$_3$, C(O)OR$^a$, C(O)N(R$^a$)$_2$ and $C_{3-6}$-cycloalkyl which is unsubstituted or substituted with $C_{1-3}$-alkyl or halo-$C_{1-3}$-alkyl.

In another embodiment in combination with any of the above or below embodiments, A in the compound according to Formula (I) is

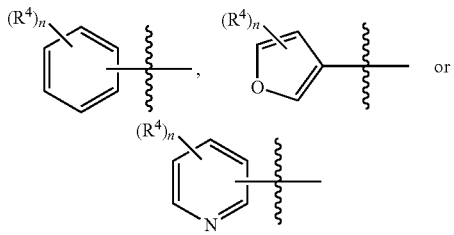

wherein

R⁴ is independently halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, S(O)$_2$N(R$^a$)$_2$ and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo;

R$^a$ is hydrogen or $C_{1-6}$-alkyl; and n is 0 to 5.

In a more preferred embodiment in combination with any of the above or below embodiments, n is 1 to 5 and R⁴ is independently selected from halogen, $C_{1-6}$-alkyl, halo-$C_{1-6}$-alkyl and $C_{3-6}$-cycloalkyl which is unsubstituted or substituted with 1 or 2 substituents independently selected from the group consisting of halogen, $C_{1-3}$-alkyl and halo-$C_{1-3}$-alkyl.

In another embodiment in combination with any of the above or below embodiments, A in the compound according to Formula (I) is

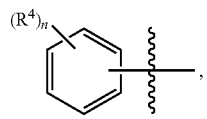

wherein

R⁴ is independently halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, S(O)$_2$N(R$^a$)$_2$, and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo;

R$^a$ is hydrogen or $C_{1-6}$-alkyl, and n is 0 to 5.

In another embodiment in combination with any of the above or below embodiments, A in the compound according to Formula (I) is

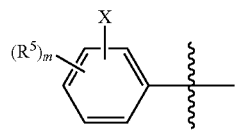

wherein

X is halogen, $C_{1-6}$-alkyl or cyclopropyl, wherein and the alkyl and cycloalkyl are unsubstituted or substituted with 1 to 3 substituents independently selected from the group consisting of halogen, $C_{1-3}$-alkyl, and halo-$C_{1-3}$-alkyl;

R⁵ is independently halogen or CN; and m is 0 to 4.

In another embodiment in combination with any of the above or below embodiments, A in the compound according to Formula (I) is

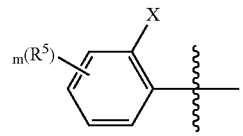

wherein X is CH$_3$, CH$_2$CH$_3$, CHF$_2$ or CF$_3$;

R⁵ is independently halogen or CN; and m is 0 to 4.

In another embodiment in combination with any of the above or below embodiments, B in the compound according to Formula (I) is a 5- or 6-membered heteroaryl containing 1 to 4 heteroatoms independently selected from N, O and S, which is unsubstituted or substituted with 1 to 5 substituents independently selected from the group consisting of halogen, OH, CN, $C_{1-6}$-alkyl, O—$C_{1-6}$-alkyl, C(O)OR$^a$, OC(O)R$^a$, S(O)—$C_{1-6}$-alkyl, S(O)$_2$—$C_{1-6}$-alkyl, N(R$^a$)$_2$, C(O)N(R$^a$)$_2$, NR$^a$C(O)—$C_{1-6}$-alkyl, S(O)$_2$N(R$^a$)$_2$, NR$^a$S(O)$_2$—$C_{1-6}$-alkyl and $C_{3-6}$-cycloalkyl, wherein the alkyl and cycloalkyl are unsubstituted or substituted with 1 to 3 substituents independently selected from the group consisting of halogen, $C_{1-3}$-alkyl, halo-$C_{1-3}$-alkyl, OH, CN and oxo; and R$^a$ is hydrogen or $C_{1-6}$-alkyl.

In another embodiment in combination with any of the above or below embodiments, B in the compound according to Formula (I) is a 5- or 6-membered heteroaryl containing 1 to 3 heteroatoms independently selected form N, O and S, which is unsubstituted or substituted with 1 to 2 substituents independently selected from the group consisting of $C_{1-6}$-alkyl, halo-$C_{1-6}$-alkyl and $C_{3-6}$-cycloalkyl.

In another embodiment in combination with any of the above or below embodiments, B in the compound according to Formula (I) is a 9- or 10-membered heteroaryl containing 1 to 4 heteroatoms independently selected from N, O and S, which is unsubstituted or substituted with 1 to 2 substituents independently selected from the group consisting of $C_{1-6}$-alkyl, halo-$C_{1-6}$-alkyl, and $C_{3-6}$-cycloalkyl or B is a 6- or 10-membered aryl, which is unsubstituted or substituted with 1 to 2 substituents independently selected from the group consisting of halogen and $C_{1-6}$-alkyl.

In another embodiment in combination with any of the above or below embodiments, B in the compound according to Formula (I) is

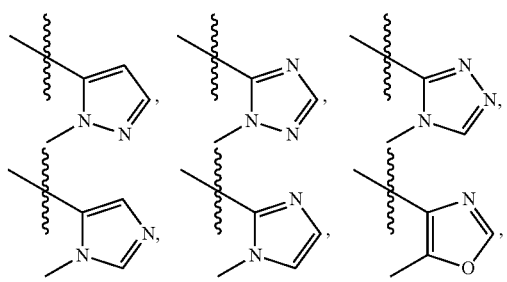

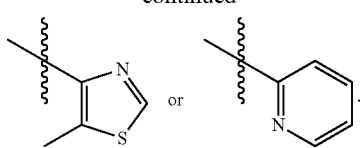 or 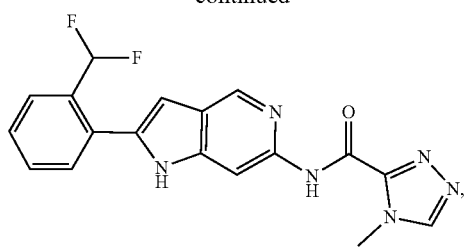
In another embodiment in combination with any of the above or below embodiments, each of $R^1$, $R^2$, $R^3$ in the compound according to Formula (I) are hydrogen.
In another embodiment in combination with any of the above or below embodiments, the compound according to Formula (I) is selected from
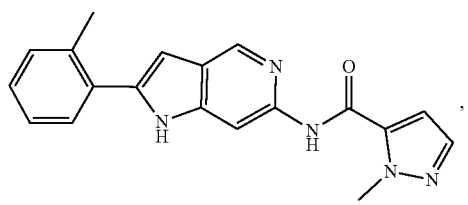,
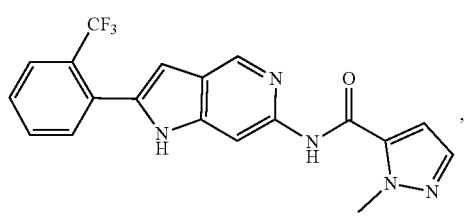,
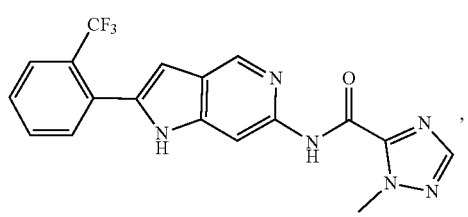,
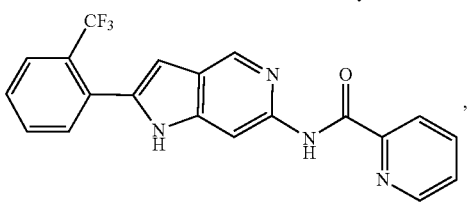,
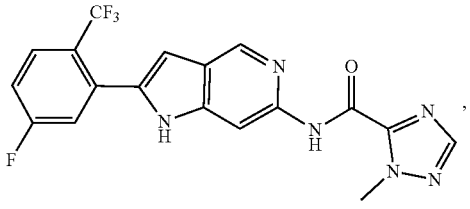,
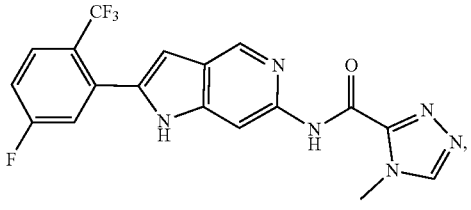,
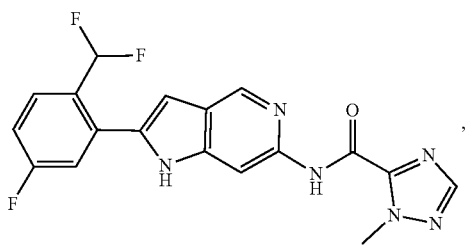,
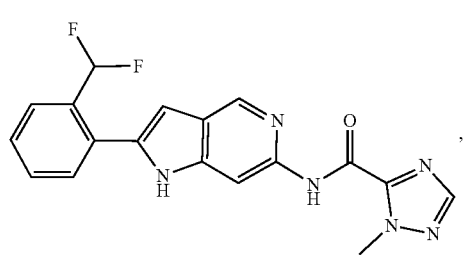 [SMILES: Cn1ncnc1C(=O)Nc1cc2[nH]c(-c3ccccc3C(F)F)c(C#N)c2cn1],
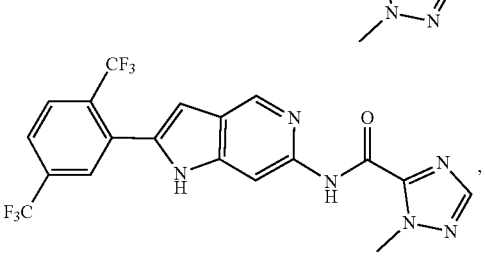,
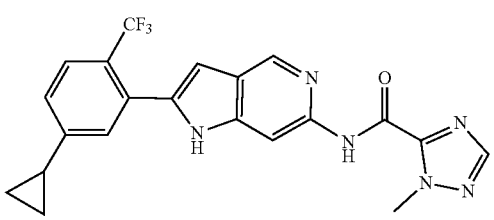,
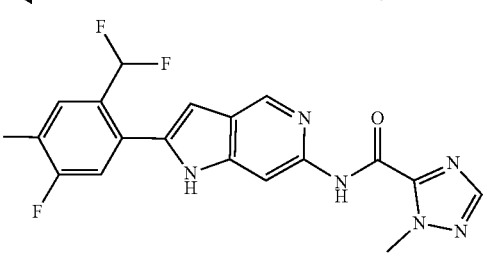, -continued
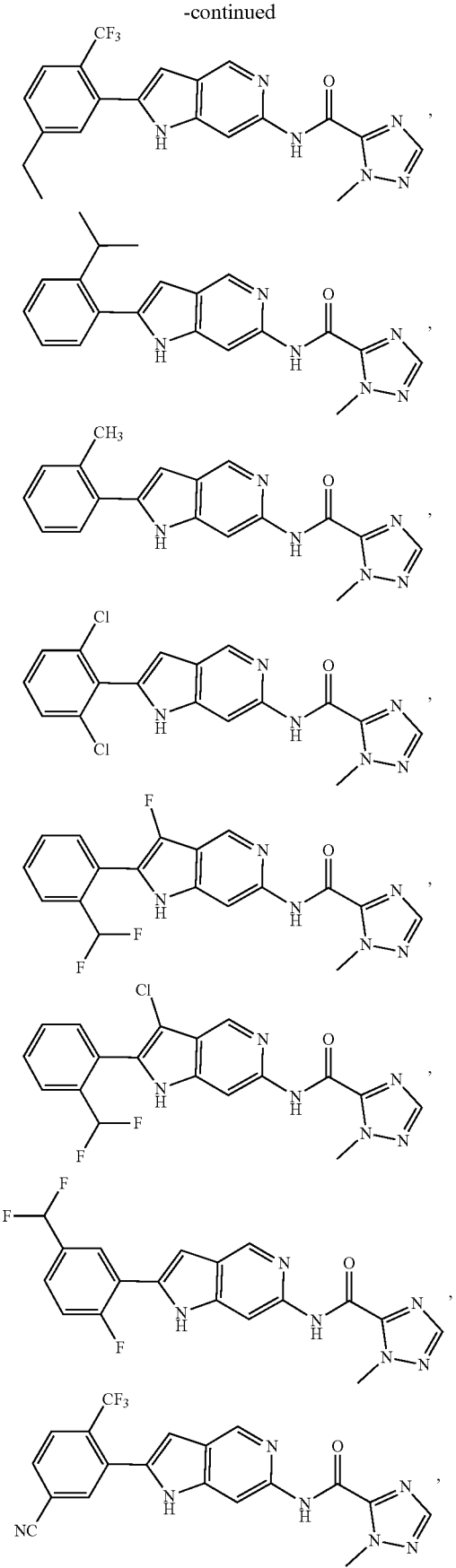
-continued
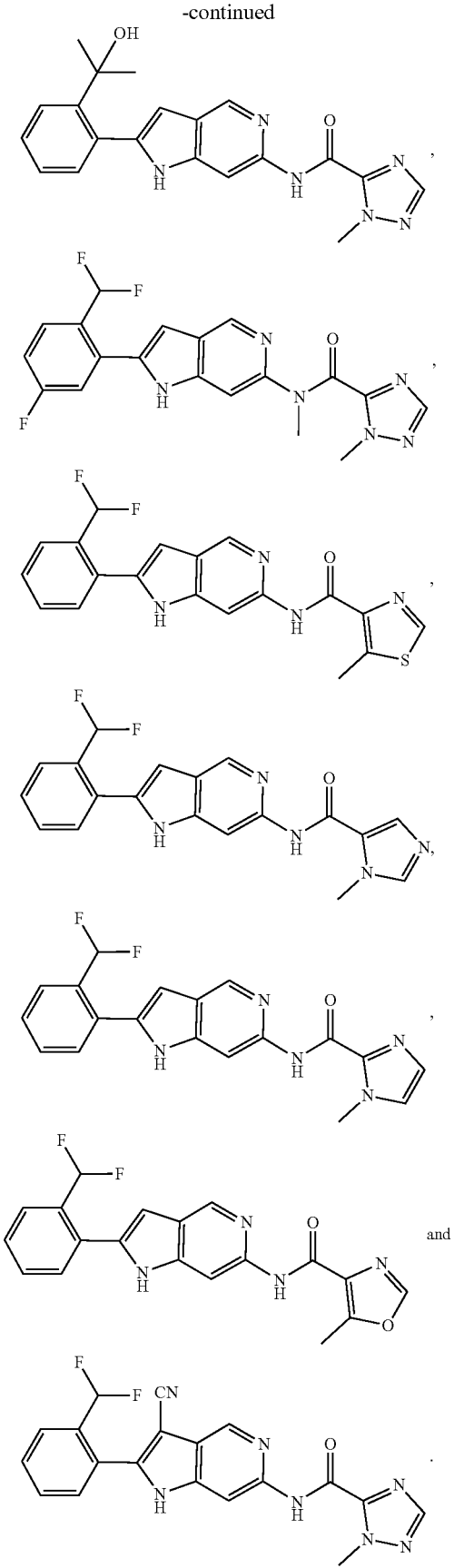

In another embodiment in combination with any of the above or below embodiments, the compound according to Formula (I) is selected from
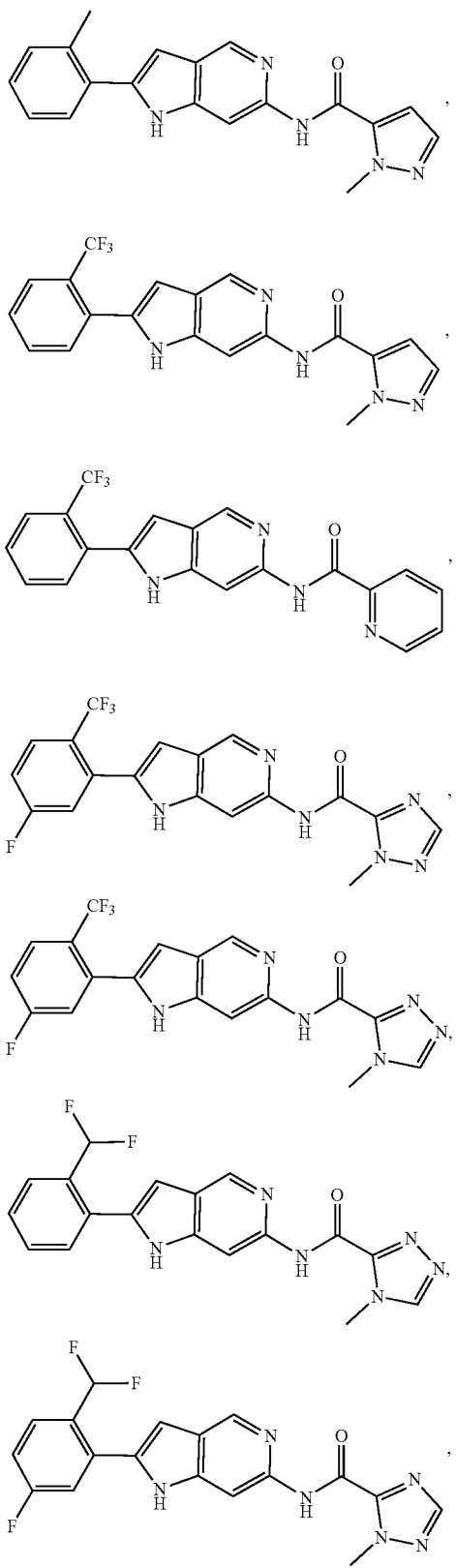
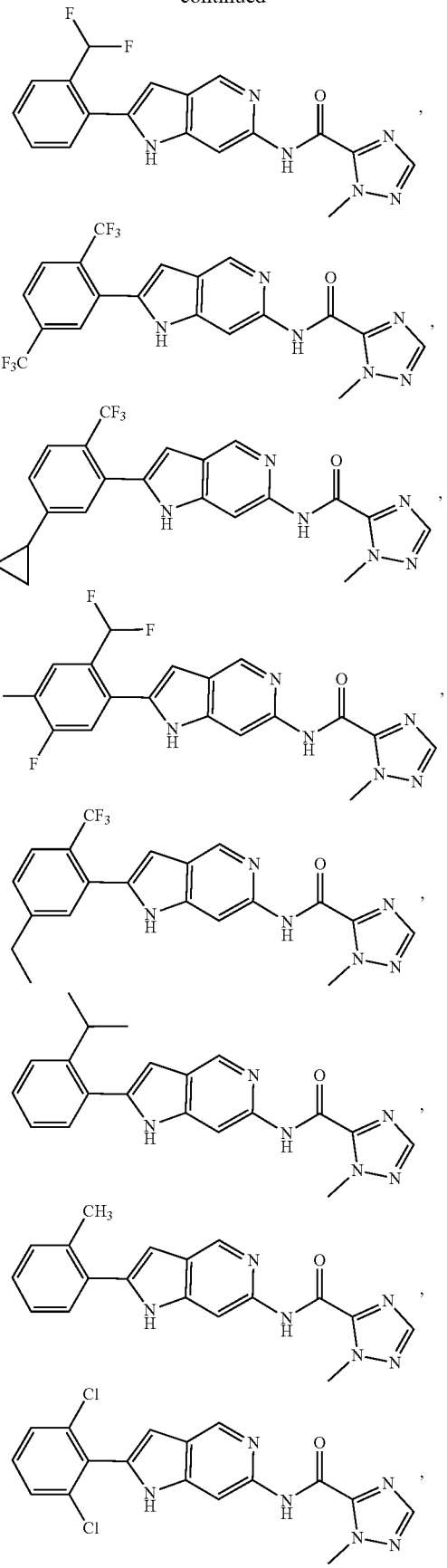

-continued

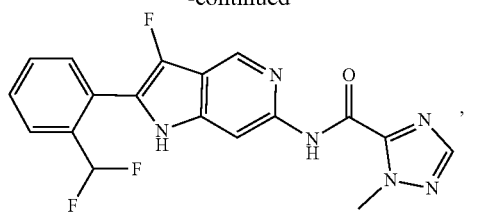,

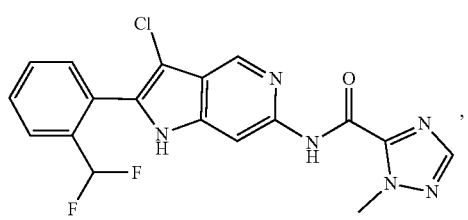,

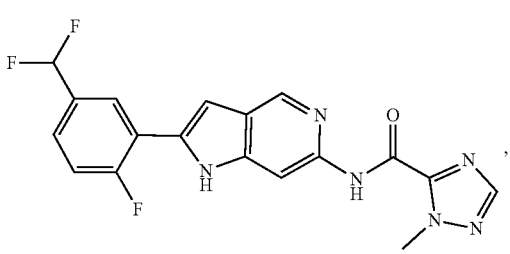,

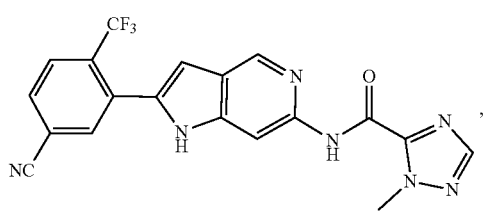,

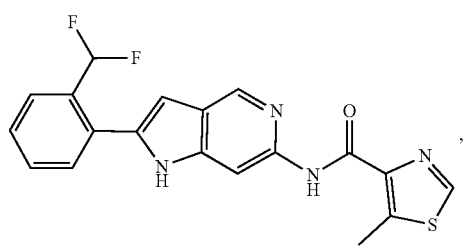,

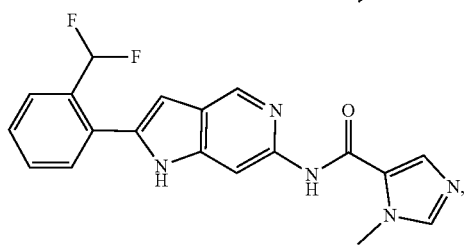,

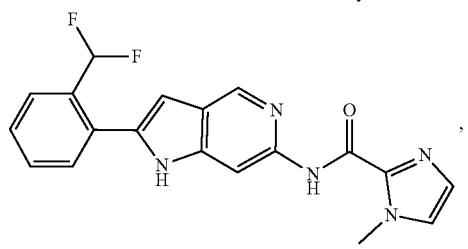,

-continued

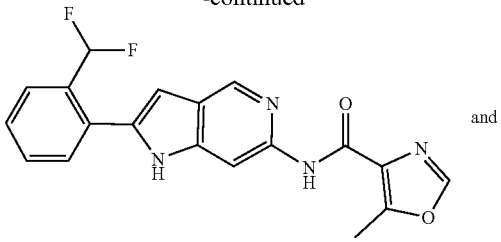 and

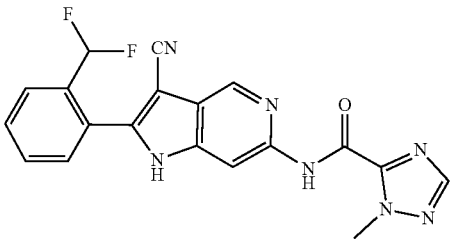.

In another embodiment, the present invention is directed to a pharmaceutical composition comprising the compound according to formula (I) and a physiologically acceptable excipient.

In another embodiment, the present invention is directed to the compound according to formula (I) for use as a medicament.

In another embodiment, the present invention is directed to the compound according to formula (I) or a pharmaceutical composition containing same and a physiologically acceptable excipient for use in the prophylaxis and/or treatment of a disease or condition mediated by aryl hydrocarbon receptor (AhR).

In another embodiment in combination with any of the above or below embodiments, the disease or condition mediated by aryl hydrocarbon receptor (AhR) is cancer.

In another embodiment in combination with any of the above or below embodiments, the compound according to formula (I) is administered with one or more therapeutic agents for cancer selected from the group consisting of PD-1 agent, PD-L1 agent, CTLA-4 agent, IDO1 inhibitor, chemotherapeutic agent, anticancer vaccine, and cytokine therapy, or wherein the compound is administered under irradiation therapy.

The compounds of the present invention share a common chemical structure according to formula (I) in claim 1.

In a preferred embodiment in combination with any of the above or below embodiments, the present invention is directed to an enantiomer, diastereomer or pharmaceutically acceptable salt of a compound according to Formula (I).

In a preferred embodiment in combination with any of the above or below embodiments, A in the compound according to Formula (I) is a 6-membered aryl or a 5- to 6-membered monocyclic heteroaryl containing 1 to 4 heteroatoms independently selected from N, O and S, wherein aryl and heteroaryl are unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, A in the compound according to Formula (I) is a 6-membered aryl substituted with 1 or 2 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, A in the compound according to Formula (I) is a 6-membered aryl or a 5- to 6-membered monocyclic heteroaryl containing 1 to 3 heteroatoms independently selected from N, O and S, wherein the aryl and heteroaryl are unsubstituted or substituted with 1 or 2 substituents independently selected from halogen, $C_{1-6}$-alkyl, and halo-$C_{1-6}$-alkyl.

In a preferred embodiment in combination with any of the above or below embodiments, A in the compound according to Formula (I) is a 6-membered monocyclic heteroaryl containing 1 to 3 nitrogen atoms, which is substituted with 1 or 2 substituents independently selected from OH, CN, halogen, $C_{1-6}$-alkyl, O—$C_{1-6}$-alkyl and $C_{3-6}$-cycloalkyl, wherein the alkyl and cycloalkyl is unsubstituted or substituted with 1 to 3 substituents independently selected from halogen and $C_{1-6}$-alkyl.

In a preferred embodiment in combination with any of the above or below embodiments, A in the compound according to Formula (I) is a 5- to 6-membered monocyclic heteroaryl containing 1 to 4 heteroatoms independently selected from N, O and S, which is substituted with 1 or 2 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, A in the compound according to Formula (I) is

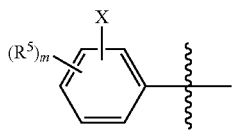

wherein
X is $CH_3$, $CH_2CH_3$, $CHF_2$ or $CF_3$;
$R^5$ is independently halogen or CN; and
m is 0 to 4.

In a preferred embodiment in combination with any of the above or below embodiments, A in the compound according to Formula (I) is

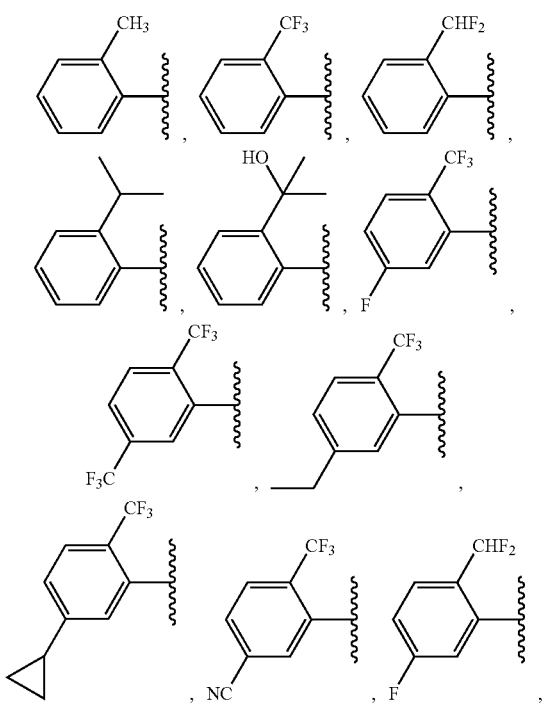

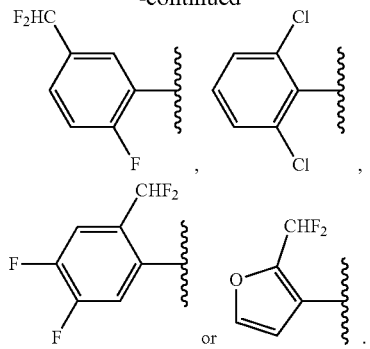

In a more preferred embodiment in combination with any of the above or below embodiments, A in the compound according to Formula (I) is

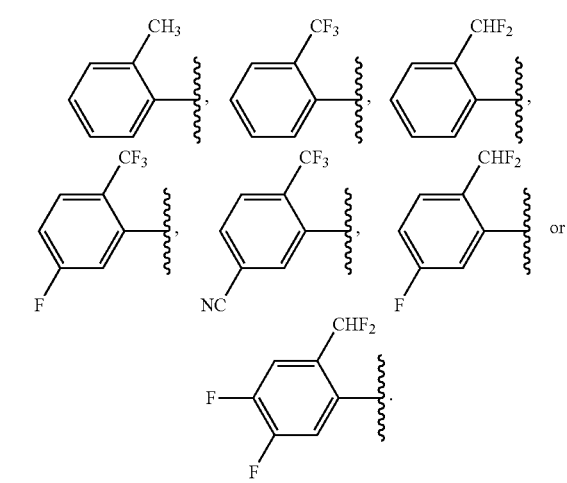

In a preferred embodiment in combination with any of the above or below embodiments, B in the compound according to Formula (I) is a 5- to 10-membered mono- or bicyclic heteroaryl containing 1 to 4 heteroatoms independently selected from N, O and S, which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, B in the compound according to Formula (I) is a 5- to 6-membered monocyclic heteroaryl containing 1 to 3 heteroatoms independently selected from N, O and S, which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl.

In a preferred embodiment in combination with any of the above or below embodiments, B in the compound according to Formula (I) is a 5- to 6-membered monocyclic heteroaryl unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl, wherein the heteroaryl has 1 to 3 heteroatoms independently selected from N, O and S, preferably N and O, and most preferably N.

In a preferred embodiment in combination with any of the above or below embodiments, B in the compound according to Formula (I) is a 5- to 6-membered monocyclic heteroaryl which is unsubstituted or substituted with 1 to 3 substituents independently selected from OH, CN, halogen, $C_{1-6}$-alkyl, and $C_{3-6}$-cycloalkyl, wherein the alkyl and cycloalkyl are unsubstituted or substituted with 1 to 3 substituents independently selected from halogen and $C_{1-6}$-alkyl, wherein the heteroaryl has 1 to 3 N atoms, preferably 2 or 3 N atoms.

In a preferred embodiment in combination with any of the above or below embodiments, B in the compound according to Formula (I) is a 5-membered heteroaryl containing 1 to 3 heteroatoms independently selected from N, O and S, which is unsubstituted or substituted with 1 or 2 substituents independently selected from $C_{1-6}$-alkyl, halo-$C_{1-6}$-alkyl and $C_{3-6}$-cycloalkyl.

In a more preferred embodiment in combination with any of the above or below embodiments, B in the compound according to Formula (I) is

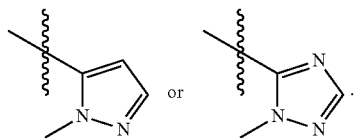

In a preferred embodiment in combination with any of the above or below embodiments, $R^1$, $R^2$, and $R^3$ in the compound according to Formula (I) are each independently selected from hydrogen, halogen, $C_{1-3}$-alkyl, OH, and CN.

In a preferred embodiment in combination with any of the above or below embodiments, one of $R^1$, $R^2$, and $R^3$ in the compound according to Formula (I) is $C_{1-3}$-alkyl, halogen, or CN, and the other two are hydrogen.

In a preferred embodiment in combination with any of the above or below embodiments, $R^1$, $R^2$, and $R^3$ in the compound according to Formula (I) are hydrogen.

In the context of the present invention "$C_{1-6}$-alkyl" means a saturated alkyl chain having 1 to 6 carbon atoms which may be straight chained or branched. Examples thereof include methyl, ethyl, propyl, isopropyl, n-butyl, isobutyl, tert-butyl, n-pentyl, isopentyl, neopentyl, and hexyl.

The term "O—$C_{1-6}$-alkyl" means that the alkyl chain is connected via an oxygen atom with the remainder of the molecule.

The term "halo-$C_{1-10}$-alkyl" means that one or more hydrogen atoms in the alkyl chain are replaced by a halogen. A preferred example thereof is $CF_3$.

A $C_{3-6}$-cycloalkyl group means a saturated or partially unsaturated mono- or bicyclic ring system comprising 3 to 6 carbon atoms. Examples include cyclopropyl, cyclobutyl, cyclopentyl, and cyclohexyl.

A 5-10-membered mono- or bicyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl, pyrazolo[1,5-a]pyrimidinyl and dibenzo[b,d]furanyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

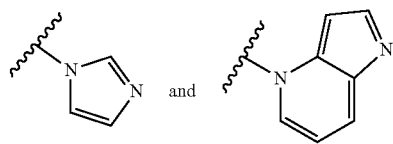 [SMILES: *n1ccnc1 ; *n1cccc2nccc1-2]

Moreover, where not explicitly defined, heteroaryl contains 1 to 4 heteroatoms independently selected from the group consisting of N, O and S.

A 6-10-membered mono- or bicyclic aromatic ring system (within the application also referred to as aryl) means an aromatic carbon cycle such as phenyl or naphthyl.

The term "halogen" comprises the specific halogen atoms fluorine, bromine, chlorine and iodine.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, fluorine and chlorine, such as, but not limited to $^2$H (deuterium, D), $^3$H (tritium), $^{11}$C, $^{13}$C, $^{14}$C, $^{15}$N, $^{18}$F, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds of Formula (I) in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g. a human. See, for example, Foster in Trends Pharmacol. Sci. 1984:5; 524. Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carboxylate in a compound of the present invention is, for example, converted into an alkyl-, aryl-, choline-, amino-, acyloxymethylester, linolenoylester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatine; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring such as cherry or orange flavour.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous, intramuscular and subcutaneous), ocular (ophthalmic), pulmonary (nasal or buccal inhalation), nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing AhR-mediated conditions for which compounds of Formula (I) are indicated, generally satisfactory results are obtained when the compounds are administered at a daily dosage of from about 0.1 mg to about 100 mg per kilogram of mammal body weight, preferably given as a single daily dose or in divided doses two to six times a day, or in sustained release form. For most large mammals, the total daily dosage is from about 1 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

ABBREVIATIONS

Herein and throughout the application, the following abbreviations may be used.
Ac acetyl
Boc tert-butyloxycarbonyl
br broad
CDI 1,1'-carbonyldiimidazole
d doublet
DAST diethylaminosulfur trifluoride
DCM dichloromethane
dba dibenzylideneacetone
DBU 1,8-diazabicyclo[5.4.0]undec-7-ene
DIBAL-H diisobutylaluminum hydride
DIPEA N, N-diisopropylethylamine
DMAP 4-(dimethylamino)pyridine
DMF N,N-dimethylformamide
DMSO dimethyl sulfoxide
dppf 1,1'-bis(diphenylphosphanyl) ferrocene
EDC 1-ethyl-3-(3-dimethylaminopropyl)carbodiimide
Et ethyl
$Et_2O$ diethyl ether
EtOAc ethyl acetate
HATU O-(7-azabenzotriazol-1-yl)-N,N,N',N'-tetramethyluronium hexafluorophosphate
HPLC high performance liquid chromatography
LDA lithium diisopropylamide
m multiplet
Me methyl
MCPBA 3-chloroperoxybenzoic acid
Ms methanesulfonyl
NBS N-bromosuccinimide
NCS N-chlorosuccinimide
PE petroleum ether
prep preparative
q quartet
rt room temperature
s singlet
SEM 2-(trimethylsilyl)ethoxymethyl
t triplet
TBAF tetra-n-butylammonium fluoride
TEA triethylamine
TFA trifluoroacetic acid
THF tetrahydrofurane
tBuXPhos 2-di-tert-butylphosphino-2',4',6'-triisopropylbiphenyl

GENERAL SCHEMES

The compounds of the present invention can be prepared by a combination of methods known in the art including the procedures described in scheme 1 below. The following reaction schemes are only meant to represent examples of the invention and are in no way meant to be a limit of the invention.

Scheme 1 describes one route of preparation for the compounds of the present invention. A substituted or unsubstituted 2-chloro-5-iodopyridin-4-amine A-1 is converted to the corresponding bis methylsulfonamide A-2 with sulfonylchloride in the presence of triethylamine. Treatment of A-2 with NaOH affords the corresponding mono methylsulfonamide A-3 which is converted to azaindole A-4 via Pd/Cu(I) catalysed coupling/cyclisation reaction with an appropriately substituted alkyne. Boc-protection to intermediate A-5 followed by Buchwald amidation affords the corresponding amide A-6. Intermediate A-6 is converted into compounds of structure A-7 by deprotection with for example TFA.

Scheme 1

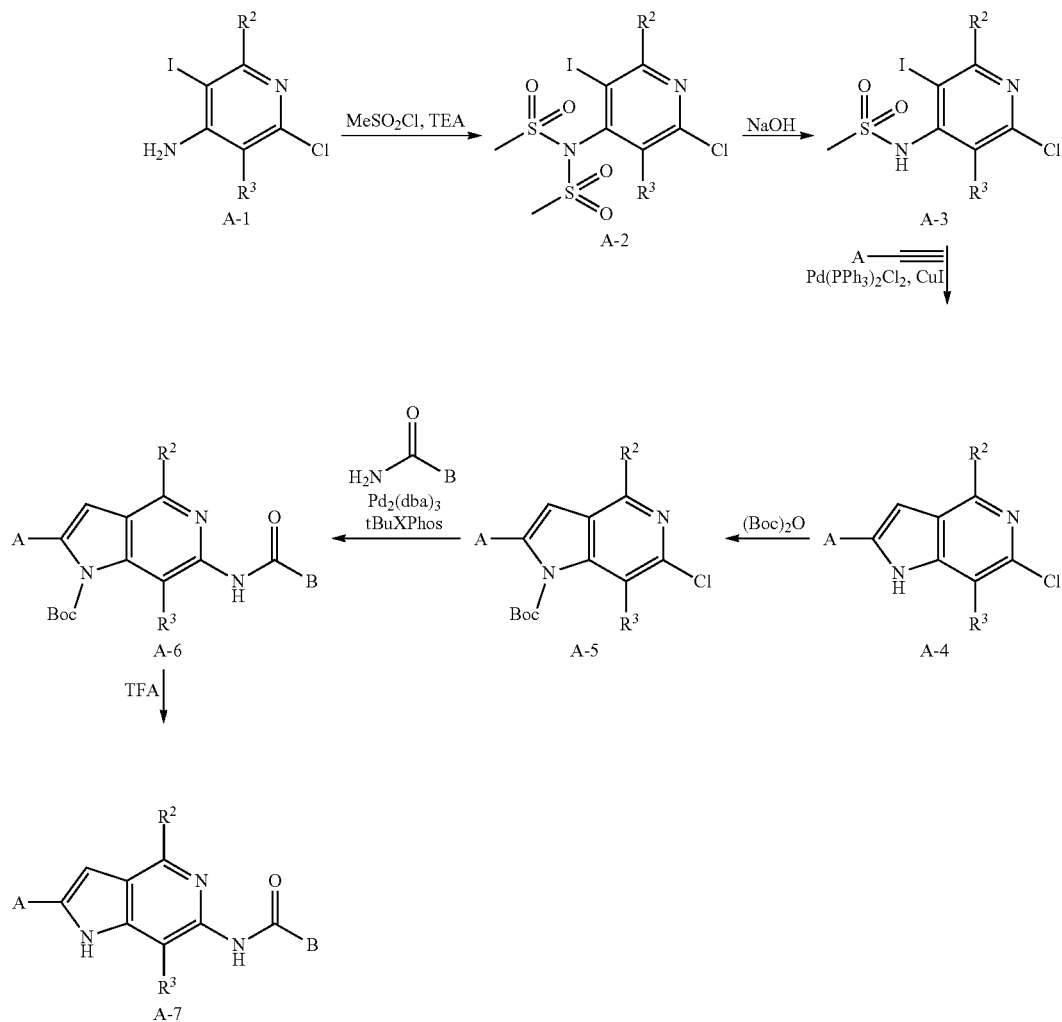

Scheme 2 describes an alternative route of preparation for the compounds of the present invention. A substituted or unsubstituted 6-chloro-1H-pyrrolo[3,2-c]pyridine B-1 is converted to the corresponding (2-trimethylsilyl)ethoxy) methyl protected intermediate B-2 through treatment with NaH and ((chloromethoxy) methyl)trimethylsilane. Intermediate B-2 can be iodinated by treatment with for example LDA at −78° C. followed by addition of iodine to give iodide B-3. Suzuki coupling of B-3 with a boronic acid or ester affords intermediates of structure B-4. Buchwald amidation with an amide gives intermediates of structure B-5 which can be deprotected with e.g. TFA to afford compounds of structure B-6. Additionally intermediate B-5 can be converted into compounds of structure B-8 in a sequence of amide hydrolysis with NaOH followed by SEM deprotection and amide coupling with a carboxylic acid.

Scheme 2

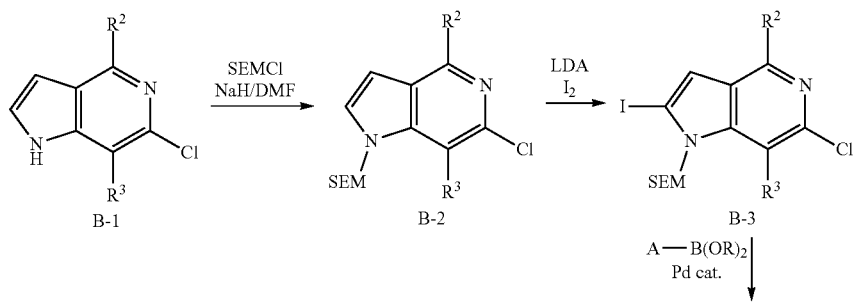

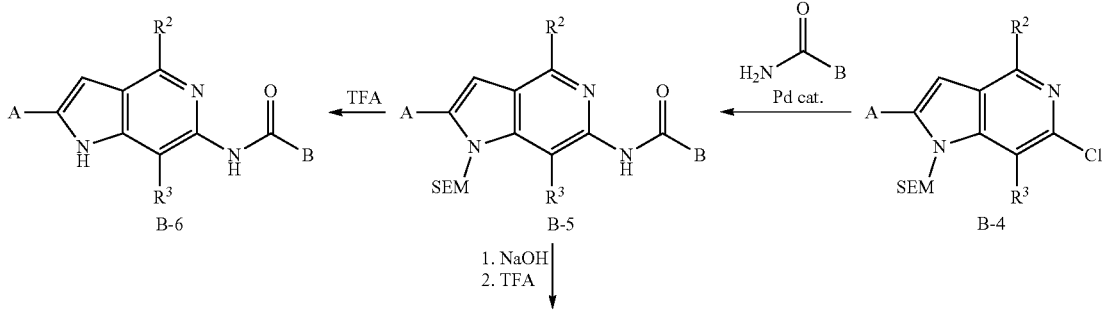

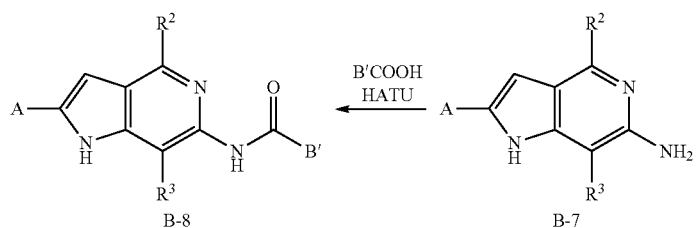

Intermediate 1:
2-Ethynyl-4-fluoro-1-(trifluoromethyl)benzene (Int 1)

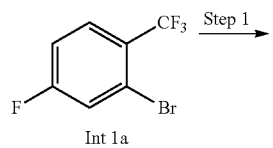

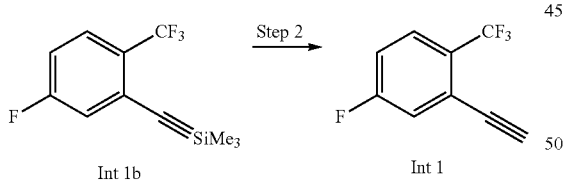

Step 1: ((5-Fluoro-2-(trifluoromethyl)phenyl)ethynyl)trimethylsilane (Int 1b)

A mixture of Pd(PPh₃)₄ (190 mg, 0.16 mmol), CuI (64 mg, 0.33 mmol), 2-bromo-4-fluoro-1-(trifluoromethyl)benzene (2.00 g, 8.26 mmol) and ethynyltrimethylsilane (2.83 g, 28.91 mmol) in TEA (20 mL) was stirred under N₂ at 70° C. overnight. The mixture was concentrated to dryness, EtOAc (20 mL) was added and the mixture was filtered through Celite®. The filtrate was concentrated to dryness and the residue was purified by column (Hexane) to give the title compound as a yellow oil.

Step 2: 2-Ethynyl-4-fluoro-1-(trifluoromethyl)benzene (Int 1)

To a mixture of ((5-fluoro-2-(trifluoromethyl)phenyl)ethynyl)trimethylsilane (Int 1b) (1.85 g, 7.11 mmol) in THF (32 mL) was added TBAF (11 mL, 1N in THF) and the mixture was stirred at rt overnight. Water was added and the mixture was extracted with EtOAc (3×50 mL). The combined organic layers were dried over anhydrous MgSO₄, filtered and concentrated to dryness. The residue was purified by column chromatography (gradient 5-100% EtOAc in PE) to give the title compound as a yellow oil.

Intermediate 1/1:
1-(Difluoromethyl)-2-ethynyl-4-fluorobenzene (Int 1/1)

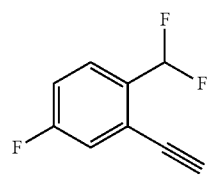

The title compound was prepared similar as described for Intermediate 1 using in step 2-bromo-1-(difluoromethyl)-4-fluorobenzene in place of 2-bromo-4-fluoro-1-(trifluoromethyl)benzene.

Intermediate 1/2: 1-(Difluoromethyl)-2-ethynylbenzene (Int 1/2)

The title compound was prepared similar as described for Intermediate 1 using in step 1 1-bromo-2-(difluoromethyl) benzene in place of 2-bromo-4-fluoro-1-(trifluoromethyl) benzene.

Intermediate 1/3: 1-Ethynyl-2-isopropylbenzene (Int 1/3)

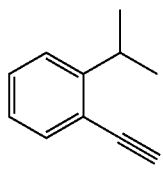

The title compound was prepared similar as described for Intermediate 1 using in step 1 1-bromo-2-isopropylbenzene in place of 2-bromo-4-fluoro-1-(trifluoromethyl) benzene.

Intermediate 1/4: 3-Ethynylfuran-2-carbaldehyde (Int 1/4)

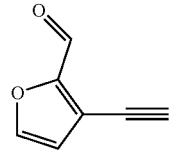

The title compound was prepared similar as described for Intermediate 1 using in Step 3-bromofuran-2-carbaldehyde in place of 2-bromo-4-fluoro-1-(trifluoromethyl)benzene.

Intermediate 1/5: 2-Ethynyl-1,4-bis(trifluoromethyl)benzene (Int 1/5)

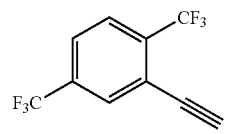

The title compound was prepared similar as described for Intermediate 1 using in Step 2-iodo-1,4-bis(trifluoromethyl) benzene in place of 2-bromo-4-fluoro-1-(trifluoro methyl) benzene.

Intermediate 2: tert-Butyl 6-chloro-2-(o-tolyl)-1H-pyrrolo[3,2-c]pyridine-1-carboxylate (Int 2)

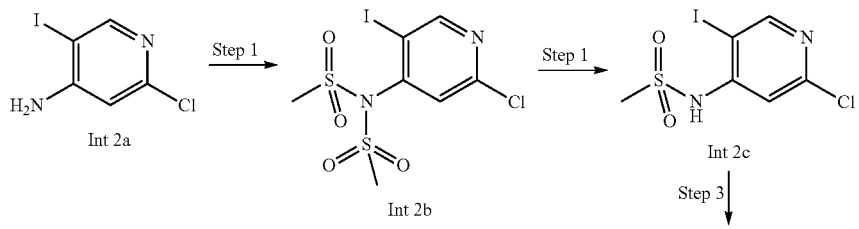

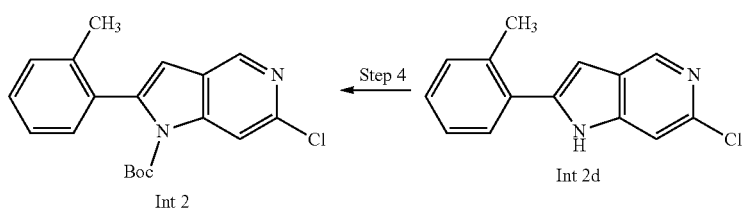

Step 1: N-(2-Chloro-5-iodopyridin-4-yl)-N-(methylsulfonyl)methanesulfonamide (Int 2b)

Methanesulfonyl chloride (2.34 mL, 30.1 mmol) in dichloromethane (5 mL) was added dropwise to a solution of 2-chloro-5-iodopyridin-4-amine (Int 2a) (1.01 g, 3.97 mmol) and triethylamine (3.73 mL, 26.4 mmol) in dichloromethane (10 mL). The mixture was allowed to warm to rt and stirred overnight. The mixture was concentrated to dryness and the residue was purified by column chromatography (gradient 5-100% EtOAc in DCM) to give the title compound as a yellow solid.

Step 2: N-(2-Chloro-5-iodopyridin-4-yl)methanesulfonamide (Int 2c)

N-(2-Chloro-5-iodopyridin-4-yl)-N-(methylsulfonyl)methanesulfonamide (Int 2b) (571 mg, 1.39 mmol) was dissolved in a mixture of aqueous NaOH solution (10 w/w %, 3.5 mL) and tetrahydrofuran (3.5 mL) and the mixture was stirred at rt for 16 h. The mixture was concentrated to dryness. Water was added and the mixture was acidified to pH 4 using aqueous citric acid solution. The precipitated solid was filtered and dried to give the title compound as a yellow solid.

Step 3: 6-Chloro-2-(o-tolyl)-1H-pyrrolo[3,2-c]pyridine (Int 2d)

A mixture of N-(2-chloro-5-iodopyridin-4-yl)methanesulfonamide (Int 2c) (1.23 g, 3.7 mmol), 1-ethynyl-2-methylbenzene (650 mg, 5.6 mmol), bis(triphenylphosphine)palladium(II) dichloride (133 mg, 0.19 mmol), copper(I) iodide (21 mg, 0.19 mmol) and triethylamine (1.69 g, 16.7 mmol) in DMF (15 mL) was stirred under nitrogen at 100° C. for 2 h. DBU (1.5 mL) was added and the mixture was stirred at 100° C. overnight. The mixture was cooled to rt, diluted with aqueous NH₄Cl solution and extracted with EtOAc. The combined organic layers were dried over anhydrous MgSO₄ and concentrated to dryness. The residue was purified by column chromatography (gradient 5-100% EtOAc in PE) to give the title compound as a yellow solid.

Step 4: tert-Butyl 6-chloro-2-(o-tolyl)-1H-pyrrolo[3,2-c]pyridine-1-carboxylate (Int 2)

To a mixture of 6-chloro-2-(o-tolyl)-1H-pyrrolo[3,2-c]pyridine (Int 2d) (525 mg, 2.2 mmol) in DCM (10 mL) a solution of di-tert-butyl dicarbonate (520 mg, 2.4 mmol) in DCM (10 mL) was added, followed by DMAP (27 mg, 0.22 mmol). The mixture was stirred at rt for 2 h. The mixture was absorbed onto silica and purified by column chromatography (DCM/EtOAc=9:1) to give the title compound as a yellow solid.

Intermediate 2/1: tert-Butyl 6-chloro-2-(2-(trifluoromethyl)phenyl)-1H-pyrrolo[3,2-c]pyridine-1-carboxylate (Int 2/1)

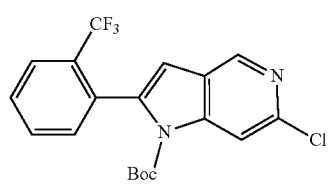 [SMILES: CC(C)(C)OC(=O)n1c(-c2ccccc2C(F)(F)F)cc2cnc(Cl)cc21]

The title compound was prepared similar as described for Intermediate 2 using in step 3 1-ethynyl-2-(trifluoromethyl)benzene in place of 1-ethynyl-2-methylbenzene.

Intermediate 2/2: tert-Butyl 6-chloro-2-(5-fluoro-2-(trifluoromethyl)phenyl)-1H-pyrrolo[3,2-c]pyridine-1-carboxylate (Int 2/2)

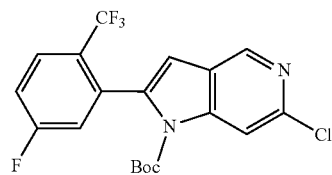

The title compound was prepared similar as described for Intermediate 2 using in step 3 2-ethynyl-4-fluoro-1-(trifluoromethyl)benzene (Int 1) in place of 1-ethynyl-2-methylbenzene.

Intermediate 2/3: tert-Butyl 6-chloro-2-(2-(difluoromethyl)-5-fluorophenyl)-1H-pyrrolo[3,2-c]pyridine-1-carboxylate (Int 2/3)

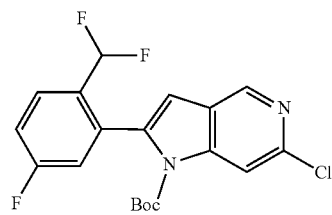 [SMILES: CC(C)(C)OC(=O)n1c(-c2cc(F)ccc2C(F)F)cc2cnc(Cl)cc21]

The title compound was prepared similar as described for Intermediate 2 using in step 3 1-(difluoromethyl)-2-ethynyl-4-fluorobenzene (Int 1/1) in place of 1-ethynyl-2-methylbenzene.

Intermediate 2/4: tert-Butyl 6-chloro-2-(2-(difluoromethyl)phenyl)-1H-pyrrolo[3,2-c]pyridine-1-carboxylate (Int 2/4)

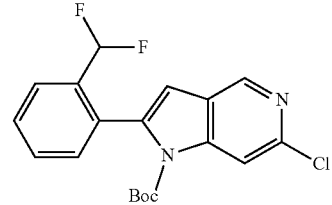 [SMILES: CC(C)(C)OC(=O)n1c(-c2ccccc2C(F)F)cc2cnc(Cl)cc21]

The title compound was prepared similar as described for Intermediate 2 using in step 3 1-(difluoromethyl)-2-ethynylbenzene (Int 1/2) in place of 1-ethynyl-2-methylbenzene.

Intermediate 2/5: tert-Butyl 2-(2,5-bis(trifluoromethyl)phenyl)-6-chloro-1H-pyrrolo[3,2-c]pyridine-1-carboxylate (Int 2/5)

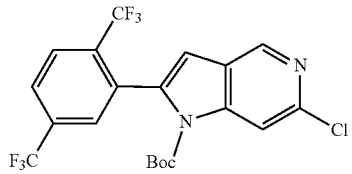 [SMILES: CC(C)(C)OC(=O)n1c(-c2cc(C(F)(F)F)ccc2C(F)(F)F)cc2cnc(Cl)cc21]

The title compound was prepared similar as described for Intermediate 2 using in step 2-ethynyl-1,4-bis(trifluoromethyl)benzene (Int 1/5) in place of 1-ethynyl-2-methylbenzene.

Intermediate 3: 1-Methyl-1H-1,2,4-triazole-5-carboxamide (Int 3)

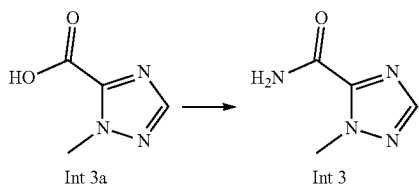

A mixture of 1-methyl-1H-1,2,4-triazole-5-carboxylic acid (7.0 g, 55.1 mmol) in SOCl$_2$ (20 mL) was heated to 70° C. for 2 h. The mixture was concentrated to dryness. The residue was dissolved in NH$_3$/MeOH (7M, 40 mL) and stirred at rt overnight. The precipitated solid was filtered off, extracted with Et$_2$O and dried under reduced pressure to give the title compound.

Intermediate 4: 4-Methyl-4H-1,2,4-triazole-3-carboxamide (Int 4)

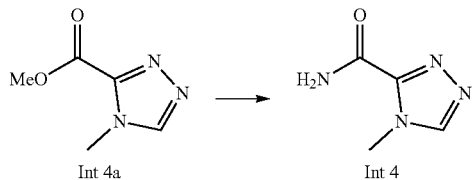

A mixture of Methyl 4-methyl-4H-1,2,4-triazole-3-carboxylate (Int 4a) (900 mg, 6.38 mmol) in NH$_3$/MeOH (7M, 15 mL) was stirred overnight at 65° C. in a sealed tube. The mixture was concentrated to half of its volume. A precipitate formed, which was filtered off, extracted with Et$_2$O and dried under reduced pressure to give the title compound.

Intermediate 5: 1,3-Dichloro-2-ethynylbenzene (Int 5)

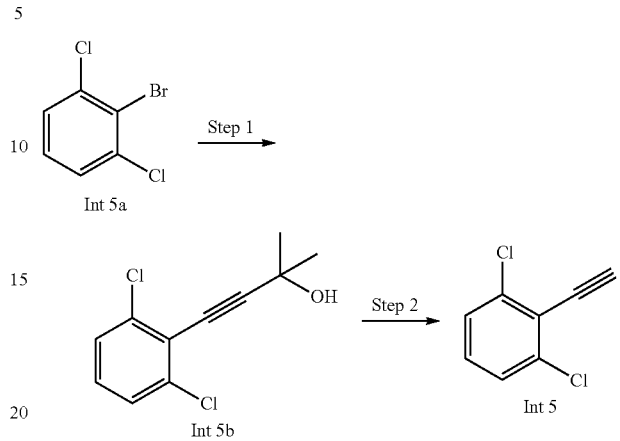

Step 1: 4-(2,6-Dichlorophenyl)-2-methylbut-3-yn-2-ol (Int 5b)

To a solution of 2-bromo-1,3-dichlorobenzene (Int 5a) (5.0 g, 22 mmol), 2-methylbut-3-yn-2-ol (2.2 g, 22 mmol), Pd(OAc)$_2$ (99 mg, 0.44 mmol) and K$_2$CO$_3$ (7.6 g, 55 mmol) in THF (50 mL) was added i-Pr$_2$NPPh$_2$ (378 mg, 1.3 mmol). The mixture was stirred at 65° C. overnight under N$_2$ in a sealed tube. The mixture was diluted with water (100 mL) and extracted with DCM (3×60 mL). The combined organic layers were washed with brine, dried over anhydrous Na$_2$SO$_4$, filtered and concentrated to dryness. The residue was purified by chromatography on silica gel (PE) to give the title compound as a colorless oil.

Step 2: 1,3-Dichloro-2-ethynylbenzene (Int 5)

A solution of 4-(2,6-dichlorophenyl)-2-methylbut-3-yn-2-ol (Int 5b) (1.1 g, 4.8 mmol) and K$_2$CO$_3$ (1.5 g, 11 mmol) in MeOH (30 mL) was stirred at rt overnight. The mixture was diluted with water and extracted with DCM (2×150 mL). The combined organic layers were washed with brine, dried over anhydrous Na$_2$SO$_4$, filtered and concentrated to dryness. The residue was purified by column chromatography on silica gel (PE) to give the title compound as a yellow solid.

Intermediate 6: tert-Butyl 6-chloro-2-(2-(difluoromethyl)furan-3-yl)-1H-pyrrolo[3,2-c]pyridine-1-carboxylate (Int 6)

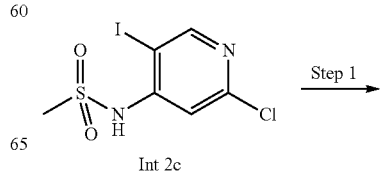

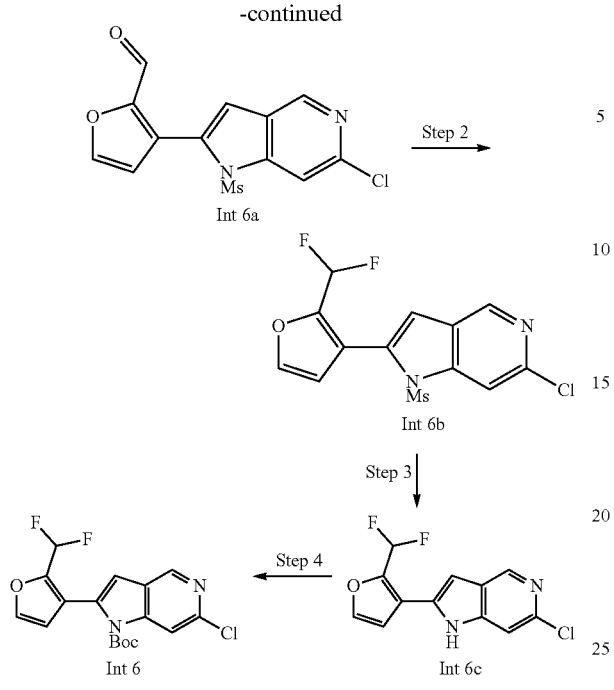

Step 1: 3-(6-Chloro-1-(methylsulfonyl)-1H-pyrrolo[3,2-c]pyridin-2-yl)furan-2-carbaldehyde (Int 6a)

To a solution of N-(2-chloro-5-iodopyridin-4-yl)methanesulfonamide (Int 2c) (761 mg, 2.30 mmol) and 3-ethynylfuran-2-carbaldehyde (Int 1/4) (275 mg, 2.30 mmol) in DMF/TEA=1:1 (10 mL) Pd(PPh$_3$)$_2$Cl$_2$ (88 mg, 0.12 mmol) and CuI (23 mg, 0.12 mmol) were added and the mixture was stirred under Ar at 100° C. overnight. The mixture was cooled to rt and water (30 mL) was added. The mixture was extracted with EtOAc (3×10 mL). The combined organic layers were washed with brine (3×15 mL), dried over anhydrous Mg$_2$SO$_4$, filtered and concentrated to dryness. The residue was purified by prep-TLC (PE/EtOAc=4:1) to give the title compound as a yellow solid.

Step 2: 6-Chloro-2-(2-(difluoromethyl)furan-3-yl)-1-(methylsulfonyl)-1H-pyrrolo[3,2-c]pyridine (Int 6b)

DAST (420 mg, 4.65 mmol) was added to a mixture of 3-(6-chloro-1-(methylsulfonyl)-1H-pyrrolo[3,2-c]pyridin-2-yl)furan-2-carbaldehyde (Int 6a) (301 mg, 0.93 mmol) in DCM (10 mL) at 0° C. and the mixture was stirred at rt for 12 h. The mixture was poured into saturated aqueous NaHCO$_3$ and extracted with EtOAc. The combined organic layers were concentrated to dryness to give the title compound as a yellow solid, which was used in the next step without further purification.

Step 3: 6-Chloro-2-(2-(difluoromethyl)furan-3-yl)-1H-pyrrolo[3,2-c]pyridine (Int 6c)

To a mixture of 6-chloro-2-(2-(difluoromethyl)furan-3-yl)-1-(methylsulfonyl)-1H-pyrrolo[3,2-c]pyridine (Int 6b) (170 mg, 0.49 mmol) in DMF (1.5 mL), was added DBU (1 mL) and the mixture was stirred at 70° C. overnight. The mixture was diluted with aqueous NH$_4$Cl solution and extracted with EtOAc. The combined organic layers were dried over anhydrous MgSO$_4$, filtered and concentrated to dryness. The residue was purified by silica gel column chromatography (EtOAc/PE=1:8) to give the title compound as a yellow solid.

Step 4: tert-Butyl 6-chloro-2-(2-(difluoromethyl)furan-3-yl)-1H-pyrrolo[3,2-c]pyridine-1-carboxylate (Int 6)

6-Chloro-2-(2-(difluoromethyl)furan-3-yl)-1H-pyrrolo[3,2-c]pyridine (Int 6c) (120 mg, 0.45 mmol) was suspended in DCM (2 mL). Di-tert-butyl dicarbonate (345 mg, 1.58 mmol) in DCM (1 mL) was added, followed by DMAP (10 mg). After evolution of carbon dioxide had ceased, the mixture was absorbed onto silica and purified by column chromatography (EtOAc/DCM=1:10) to give the title compound as white solid.

Intermediate 20: 2-(2-(6-Chloro-1-((2-(trimethylsilyl)ethoxy)methyl)-1H-pyrrolo[3,2-c]pyridin-2-yl)phenyl)propan-2-ol (Int 20)

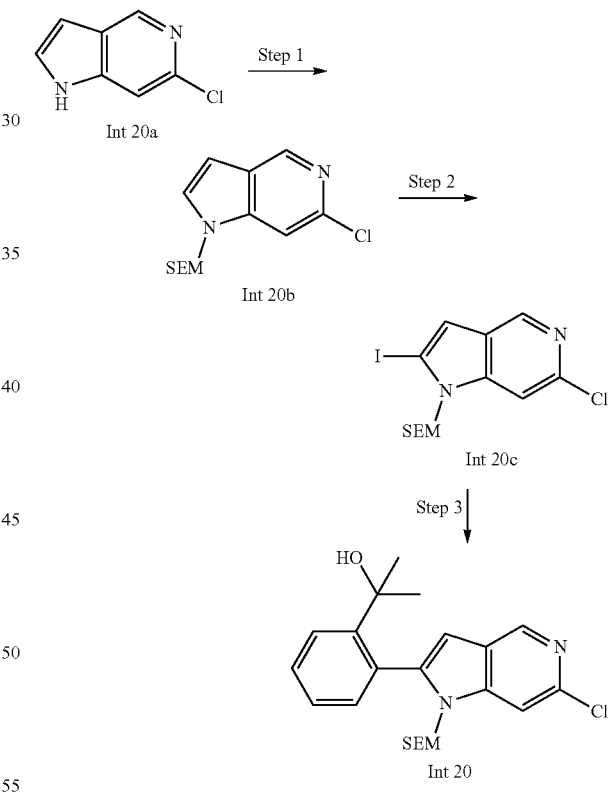

Step 1: 6-Chloro-1-((2-(trimethylsilyl)ethoxy)methyl)-1H-pyrrolo[3,2-c]pyridine (Int 20b)

NaH (395 mg, 9.9 mmol, 60% in mineral oil) was added to a mixture of 6-chloro-1H-pyrrolo[3,2-c]pyridine (500 mg, 3.3 mmol) in THF (30 mL) at 0° C. After stirring for 1 h at 0° C., SEM-Cl (824 mg, 4.9 mmol) was added at the same temperature and the mixture was stirred for 2 h at 0° C. The mixture was quenched with H$_2$O (45 mL) and extracted with DCM (2×50 mL). The combined organic layers were washed with brine, dried over anhydrous Na$_2$SO$_4$, filtered and concentrated to dryness. The residue was purified by column chromatography on silica gel (PE/EtOAc=10:1) to give the title compound as a yellow oil.

Step 2: 6-Chloro-2-iodo-1-((2-(trimethylsilyl) ethoxy)methyl)-1H-pyrrolo[3,2-c]pyridine (Int 20c)

A mixture of 2-(2-(6-chloro-1-((2-(trimethylsilyl)ethoxy)methyl)-1H-pyrrolo[3,2-c]pyridin-2-yl)phenyl)propan-2-ol (Int 20b) (600 mg, 2.1 mmol) and LDA (3 mL, 1.0 mol/L in THF) in THF (30 mL) was stirred at −78° C. After stirring for 1 h at −78° C., I$_2$ (690 mg, 2.7 mmol) was added and the mixture was stirred for 1 h at the same temperature. The mixture was allowed warm to rt and stirred overnight. The mixture was quenched with aqueous NH$_4$Cl solution (40 mL) and extracted with DCM (3×50 mL). The combined organic layers were washed with brine, dried over anhydrous Na$_2$SO$_4$, filtered and concentrated to dryness. The residue was purified by column chromatography on silica gel (PE/EA=10:1) to give the title compound as a white solid.

Step 3: 2-(2-(6-Chloro-1-((2-(trimethylsilyl)ethoxy)methyl)-1H-pyrrolo[3,2-c]pyridin-2-yl)phenyl)propan-2-ol (Int 20)

A mixture of 6-chloro-2-iodo-1-((2-(trimethylsilyl)ethoxy)methyl)-1H-pyrrolo[3,2-c]pyridine (Int 20c) (189 mg, 0.46 mmol), 3,3-dimethylbenzo[c][1,2]oxaborol-1(3H)-ol (150 mg, 0.92 mmol), PdCl$_2$(dppf)CH$_2$Cl$_2$ (74 mg, 0.09 mmol), n-Bu$_4$NBr (148 mg, 0.06 mmol) and Na$_2$CO$_3$ (394 mg, 0.37 mmol) in DMF/H$_2$O (15 mL/3 mL) was stirred at 80° C. under N$_2$ for 6 h. The mixture was extracted with DCM (2×75 mL). The combined organic layers were washed with brine, dried over anhydrous Na$_2$SO$_4$, filtered and concentrated to dryness. The residue was purified by column chromatography on silica gel (PE/EA=3:1) to give the title compound as a white solid.

Intermediates 20/1 to 20/2

The following Intermediates were prepared similar as described for Intermediate 20 using the appropriate Suzuki coupling building blocks.

Intermediate 21: 6-Chloro-2-(2-isopropylphenyl)-1-((2-(trimethylsilyl)ethoxy) methyl)-1H-pyrrolo[3,2-c]pyridine (Int 21)

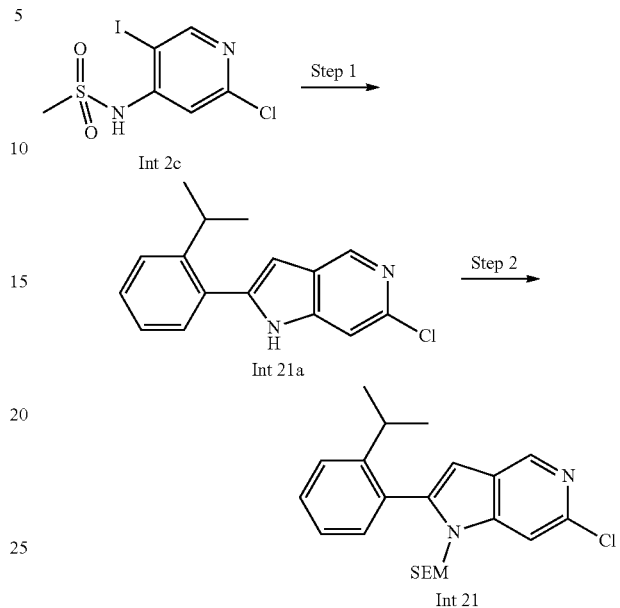

Step 1: 6-Chloro-2-(2-isopropylphenyl)-1H-pyrrolo[3,2-c]pyridine (Int 21a)

To a solution of 1-ethynyl-2-isopropylbenzene (Int 1/3) (325 mg, 2.3 mmol), N-(2-chloro-5-iodopyridin-4-yl)methanesulfonamide (Int 2c) (500 mg, 1.5 mmol), Pd(PPh$_3$)Cl$_2$ (105 mg, 0.15 mmol) and CuI (30 mg, 0.15 mmol) in DMF (25 mL) was added Et$_3$N (750 mg, 7.5 mmol). The mixture was stirred at 100° C. under N$_2$ for 3 h. DBU (2.5 mL) was added and the mixture was stirred at 100° C. overnight. The mixture was diluted with water (80 mL) and extracted with DCM (3×50 mL). The combined organic layers were washed with brine, dried over anhydrous Na$_2$SO$_4$, filtered and concentrated to dryness. The residue was purified by column chromatography on silica gel (PE/EtOAc=10:1) to give the title compound as a yellow solid.

| Int. # | Suzuki coupling building block | Structure |
|---|---|---|
| Int 20/1 | (structure: 5-(difluoromethyl)-2-fluorophenyl boronic acid pinacol ester) | (structure: 2-(5-(difluoromethyl)-2-fluorophenyl)-6-chloro-1-SEM-pyrrolo[3,2-c]pyridine) |
| Int 20/2 | (structure: 5-cyano-2-(trifluoromethyl)phenyl boronic acid pinacol ester) | (structure: 2-(5-fluoro-2-cyanophenyl)-6-chloro-1-SEM-pyrrolo[3,2-c]pyridine) |

Step 2: 6-Chloro-2-(2-isopropylphenyl)-1-((2-(trimethylsilyl)ethoxy)methyl)-1H-pyrrolo [3,2-c]pyridine (Int 21)

A mixture of 6-chloro-2-(2-isopropylphenyl)-1H-pyrrolo [3,2-c]pyridine (Int 21a) (200 mg, 0.74 mmol) and NaH (74 mg, 1.9 mmol, 60% in mineral oil) in THF (15 mL) was stirred at 0° C. for 1 h. SEM-Cl (184 mg, 1.1 mmol) was added and the mixture was stirred for 2 h at 0° C. Saturated aqueous NH$_4$Cl (30 mL) was added and the mixture was extracted with DCM (2×50 mL). The combined organic layers were washed with brine, dried over anhydrous Na$_2$SO$_4$, filtered and concentrated to dryness. The residue was purified by prep-TLC (PE/EtOAc=5:1) to give the title compound as a yellow solid.

Intermediates 21/1 to 21/2

The following Intermediates were prepared similar as described for Intermediate 21 using the appropriate building blocks.

| Int. # | Building block | Structure |
|---|---|---|
| Int 21/1 | 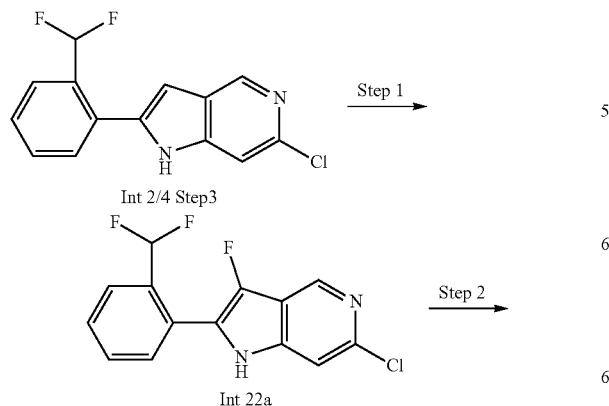 | 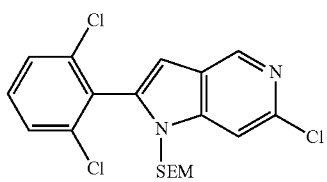 [SMILES: C[Si](C)(C)CCOCn1c(-c2c(Cl)cccc2Cl)cc2cnc(Cl)cc21] |
| Int 21/2 | | 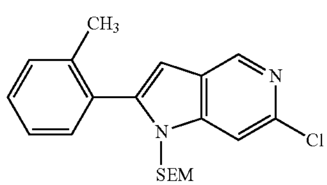 [SMILES: Cc1ccccc1-c1cc2cnc(Cl)cc2n1COCC[Si](C)(C)C] |

Intermediate 22: 6-Chloro-2-(2-(difluoromethyl) phenyl)-3-fluoro-1-((2-(trimethylsilyl)ethoxy) methyl)-1H-pyrrolo[3,2-c]pyridine (Int 22)

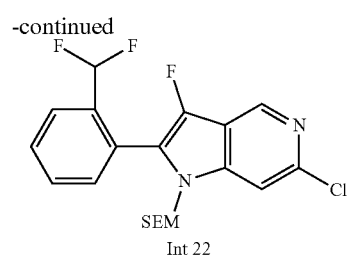

Step 1: 6-Chloro-2-(2-(difluoromethyl)phenyl)-3-fluoro-1H-pyrrolo[3,2-c]pyridine (Int 22a)

A solution of 6-chloro-2-(2-(difluoromethyl)phenyl)-1H-pyrrolo[3,2-c]pyridine (Int 2/4 Step 3) (650 mg, 9.0 mmol) and select flour (980 mg, 2.8 mmol) in DMF (550 mL) was stirred at rt under N$_2$ overnight. The mixture was concentrated to half of the volume and water (300 mL) was added. The mixture was extracted with DCM (3×60 mL). The combined organic layers were washed with brine, dried over anhydrous Na$_2$SO$_4$, filtered and concentrated to dryness. The residue was purified by prep-HPLC to give the title compound as a yellow solid.

Step 2: 6-Chloro-2-(2-(difluoromethyl)phenyl)-3-fluoro-1-((2-(trimethylsilyl)ethoxy) methyl)-1H-pyrrolo[3,2-c]pyridine (Int 22)

A mixture of 6-chloro-2-(2-(difluoromethyl)phenyl)-3-fluoro-1H-pyrrolo[3,2-c]pyridine (Int 22a) (190 mg, 0.64 mmol) and NaH (128 mg, 3.2 mmol, 60% in mineral oil) in THF (25 mL) was stirred at 0° C. for 1 h. SEM-Cl (214 mg, 1.3 mmol) was added and the mixture was stirred for 2 h at 0° C. Saturated aqueous NH$_4$Cl (20 mL) was added and the mixture was extracted with DCM (3×55 mL). The combined organic layers were washed with brine, dried over anhydrous Na$_2$SO$_4$, filtered and concentrated to dryness. The residue was purified by column chromatography on silica gel (PE/EtOAc=5:1) to give the title compound as a yellow oil.

Intermediate 23: 3,6-Dichloro-2-(2-(difluoromethyl) phenyl)-1-((2-(trimethylsilyl) ethoxy)methyl)-1H-pyrrolo[3,2-c]pyridine (Int 23)

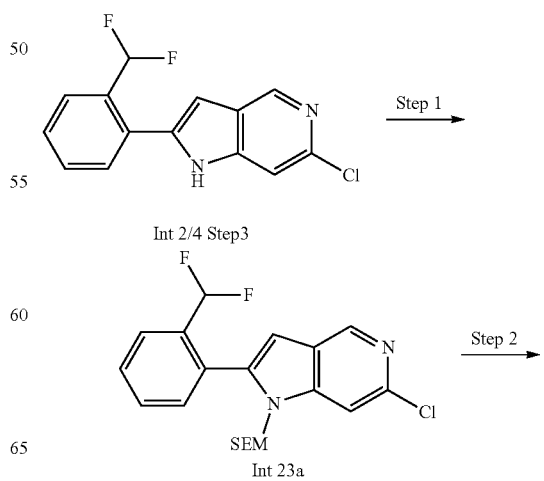

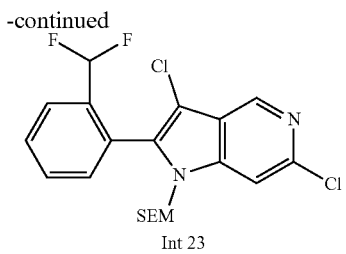

Int 23

Step 1: 6-Chloro-2-(2-(difluoromethyl)phenyl)-1-((2-(trimethylsilyl)ethoxy)methyl)-1H-pyrrolo[3,2-c]pyridine (Int 23a)

A mixture of 6-chloro-2-(2-(difluoromethyl)phenyl)-1H-pyrrolo[3,2-c]pyridine (Int 2/4 Step 3) (555 mg, 2.0 mmol) and NaH (399 mg, 10 mmol, 60% in mineral oil) in THF (25 mL) was stirred at 0° C. for 1 h. SEM-Cl (664 mg, 4.0 mmol) was added and the mixture was stirred for 2 h at the same temperature. Saturated aqueous $NH_4Cl$ (30 mL) was added and the mixture was extracted with DCM (2×80 mL). The combined organic layers were washed with brine, dried over anhydrous $Na_2SO_4$, filtered and concentrated to dryness. The residue was purified by column chromatography on silica gel (PE/EtOAc=5:1) to give the title compound as a yellow oil.

Step 2: 3,6-Dichloro-2-(2-(difluoromethyl)phenyl)-1-((2-(trimethylsilyl)ethoxy) methyl)-1H-pyrrolo[3,2-c]pyridine (Int 23)

A solution of 6-chloro-2-(2-(difluoromethyl)phenyl)-1-((2-(trimethylsilyl)ethoxy) methyl)-1H-pyrrolo[3,2-c]pyridine (Int 23a) (430 mg, 1.1 mmol) and NCS (168 mg, 1.3 mmol) in DMF (15 mL) was stirred at 60° C. for 3 h. The mixture was diluted with water (100 mL) and extracted with DCM (2×50 mL). The combined organic layers were washed with brine, dried over anhydrous $Na_2SO_4$, filtered and concentrated to dryness. The residue was purified by column chromatography on silica gel (PE/EtOAc=5:1) to give the title compound as a yellow oil.

Intermediate 24: 2-(2-(Difluoromethyl)phenyl)-1H-pyrrolo[3,2-c]pyridin-6-amine (Int 24)

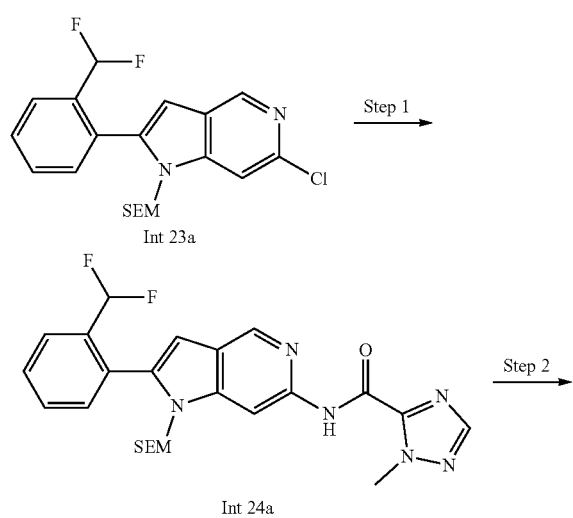

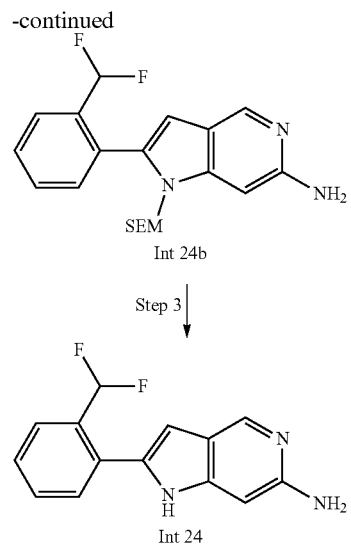

Int 24

Step 1: N-(2-(2-(Difluoromethyl)phenyl)-1-((2-(trimethylsilyl)ethoxy)methyl)-1H-pyrrolo[3,2-c]pyridin-6-yl)-1-methyl-1H-1,2,4-triazole-5-carboxamide (Int 24a)

A solution of 6-chloro-2-(2-(difluoromethyl)phenyl)-1-((2-(trimethylsilyl)ethoxy) methyl)-1H-pyrrolo[3,2-c]pyridine (Int 23a) (1.0 g, 2.5 mmol), 1-methyl-1H-1,2,4-triazole-5-carboxamide (Int 3) (470 mg, 3.7 mmol), $Pd_2(dba)_3$ (449 mg, 0.49 mmol), tBuXPhos (312 mg, 0.74 mmol) and $K_2CO_3$ (1.4 g, 10 mmol) in DMF (10 mL) was stirred at 130° C. overnight in a sealed tube. The mixture was diluted with water (50 mL) and extracted with DCM (3×60 mL). The combined organic layers were washed with brine, dried over $Na_2SO_4$, filtered and concentrated to dryness. The residue was purified by silica gel column chromatography (PE/EtOAc=5:1) to give the title compound as a yellow solid.

Step 2: 2-(2-(Difluoromethyl)phenyl)-1-((2-(trimethylsilyl)ethoxy)methyl)-1H-pyrrolo[3,2-c]pyridin-6-amine (Int 24b)

A solution of N-(2-(2-(difluoromethyl)phenyl)-1-((2-(trimethylsilyl)ethoxy)methyl)-1H-pyrrolo[3,2-c]pyridin-6-yl)-1-methyl-1H-1,2,4-triazole-5-carboxamide (Int 24a) (220 mg, 0.44 mmol) and NaOH (88 mg, 2.2 mmol) in MeOH/$H_2O$ (30/10 mL) was stirred at 90° C. for 7 h. The mixture was diluted with water (50 mL) and extracted with DCM (3×60 mL). The combined organic layers were washed with brine, dried over anhydrous $Na_2SO_4$, filtered and concentrated to dryness to give the title compound as a yellow oil.

Step 3: 2-(2-(Difluoromethyl)phenyl)-1H-pyrrolo[3,2-c]pyridin-6-amine (Int 24)

A solution of 2-(2-(difluoromethyl)phenyl)-1-((2-(trimethylsilyl)ethoxy)methyl)-1H-pyrrolo[3,2-c]pyridin-6-amine (Int 24b) (170 mg, 0.437 mmol) in DCM (10 mL)/TFA (10 mL) was stirred at 50° C. for 2 h. The solvents were removed under reduced pressure. The residue was redissolved in acetonitrile/$H_2O$ (20 mL/4 mL), $K_2CO_3$ (301 mg, 2.2 mmol) was added, and the mixture was stirred for 1 h at the same temperature. Water (30 mL) was added and the mixture was extracted with DCM (2×50 mL). The combined organic layers were washed with brine, dried over anhydrous $Na_2SO_4$, filtered and concentrated to dryness. The residue was purified by prep-TLC (DCM/MeOH=20:1) to give the title compound as a white solid.

Intermediate 25: tert-Butyl 6-chloro-2-(5-cyclopropyl-2-(trifluoromethyl)phenyl)-1H-pyrrolo[3,2-c]pyridine-1-carboxylate (Int 25)

mixture was concentrated and EtOAc (80 mL) was added. The mixture filtered through Celite®. The filtrate was concentrated to dryness and the residue was purified by column chromatography (PE) to give the title compound as colorless oil.

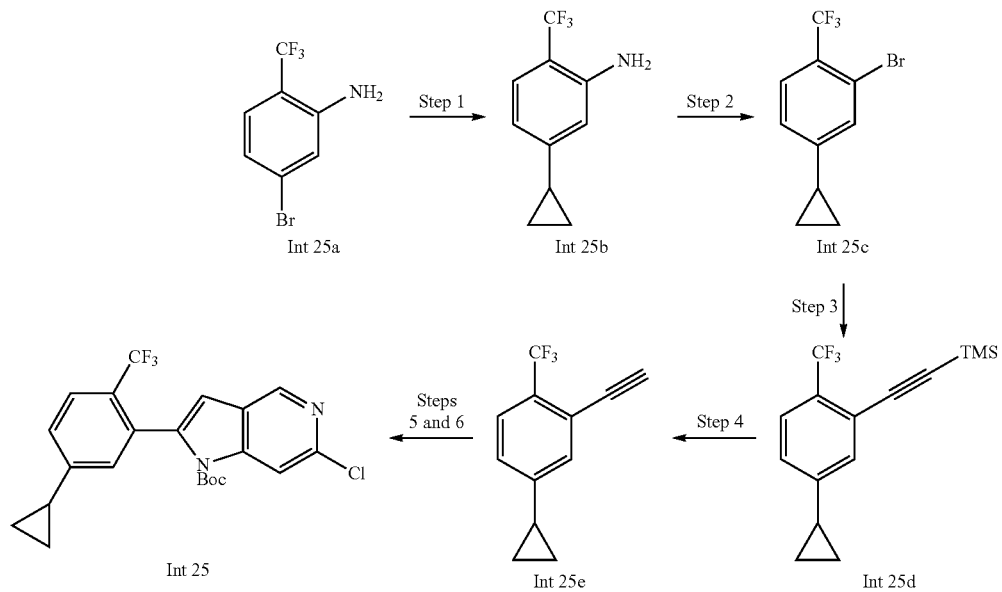

Step 1: 5-Cyclopropyl-2-(trifluoromethyl)aniline (Int 25b)

Pd(dppf)Cl$_2$ (613 mg, 0.84 mmol) was added to a mixture of 5-bromo-2-(trifluoromethyl)aniline (Int 25a) (2.00 g, 8.37 mmol), cyclopropylboronic acid (929 mg, 12.56 mmol) and Na$_2$CO$_3$ (1.77 g, 16.70 mmol) in dioxane (25 mL) and the mixture was stirred at 90° C. overnight. The mixture was concentrated to dryness and the residue was purified by column chromatography (0-2% EtOAc in PE) to give the title compound as yellow oil.

Step 2: 2-Bromo-4-cyclopropyl-1-(trifluoromethyl)benzene (Int 25c)

tert-Butyl nitrite (1.69 g, 16.41 mmol) was quickly added to a solution of 5-cyclopropyl-2-(trifluoromethyl)aniline (Int 25b) (1.10 g, 5.47 mmol) in CH$_3$CN (50 mL) and the mixture was stirred at rt under N$_2$ for 2 min. CuBr$_2$ (3.02 g, 13.66 mmol) was added and the mixture was stirred at rt under N$_2$ for 3 h. Water (20 mL) was added and the mixture was extracted with EtOAc (2×50 mL). The combined organic layers were concentrated to dryness and the residues was purified by column chromatography (0-2% DCM) to give the title compound as colorless oil.

Step 3: ((5-Cyclopropyl-2-(trifluoromethyl)phenyl)ethynyl)trimethylsilane (Int 25d)

To a mixture of Pd(PPh$_3$)$_4$ (307 mg, 0.26 mmol) and CuI (101 mg, 0.53 mmol) in TEA (20 mL) were added 2-bromo-4-cyclopropyl-1-(trifluoromethyl)benzene (Int 25c) (1.40 g, 5.28 mmol) and ethynyl trimethylsilane (1.82 g, 18.57 mmol). The mixture was stirred at 70° C. overnight. The Step 4: 4-Cyclopropyl-2-ethynyl-1-(trifluoromethyl)benzene (Int 25e)

To a solution of ((5-cyclopropyl-2-(trifluoromethyl)phenyl)ethynyl)trimethylsilane (Int 23d) in MeOH (5 mL) was added K$_2$CO$_3$ (582 mg, 4.22 mmol) and the mixture was stirred at rt for 0.5 h. The mixture was poured into ice-water and extracted with diethyl ether (2×30 mL). The combined organic layers were dried over anhydrous MgSO$_4$, filtered and concentrated to dryness to afford the title compound.

Steps 5-6: tert-Butyl 6-chloro-2-(5-cyclopropyl-2-(trifluoromethyl)phenyl)-1H-pyrrolo[3,2-c]pyridine-1-carboxylate (Int 25)

The title compound was prepared similar as described for Intermediate 2 steps 3 and 4 using in step 3 4-cyclopropyl-1-ethynyl-2-(trifluoromethyl)benzene (Int 25e) in place of 1-ethynyl-2-methylbenzene.

Intermediate 25/1: tert-Butyl 6-chloro-2-(5-ethyl-2-(trifluoromethyl)phenyl)-1H-pyrrolo[3,2-c]pyridine-1-carboxylate (Int 25/1)

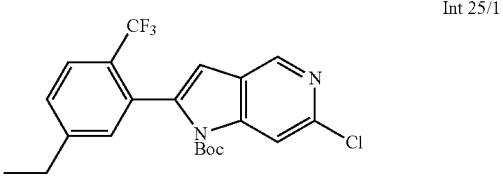 [SMILES: CCc1ccc(C(F)(F)F)c(-c2cc3cnc(Cl)cc3n2C(=O)OC(C)(C)C)c1]

The title compound was prepared similar as described for Intermediate 25 using in step 1 ethylboronic acid in place of cyclopropylboronic acid.

Intermediate 26: tert-Butyl 6-chloro-2-(2-(difluoromethyl)-4,5-difluorophenyl)-1H-pyrrolo[3,2-c]pyridine-1-carboxylate (Int 26)

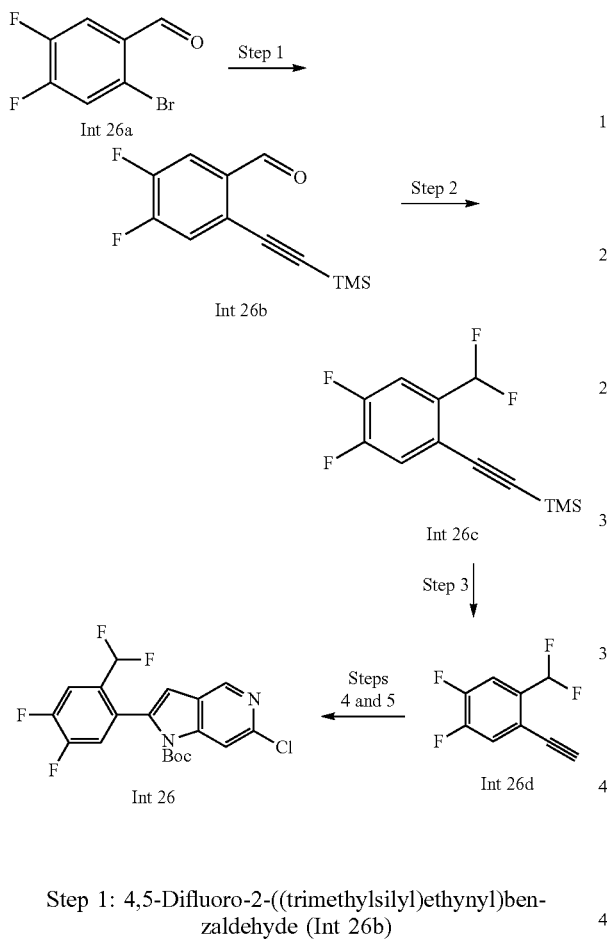

Step 1: 4,5-Difluoro-2-((trimethylsilyl)ethynyl)benzaldehyde (Int 26b)

A mixture of Pd(PPh$_3$)$_4$ (260 mg, 0.23 mmol), CuI (43 mg, 0.23 mmol), 2-bromo-4,5-difluorobenzaldehyde (1.00 g, 4.50 mmol) and ethynyl trimethylsilane (1.55 g, 15.80 mmol) in TEA (10 mL) was stirred at 70° C. overnight. The mixture was concentrated to dryness. EtOAc (20 mL) was added and the mixture was filtered through a pad of Celite®. The mixture was concentrated to dryness and the residue was purified by column chromatography (gradient 5-30% EtOAc in PE) to give the title compound as a yellow oil.

Step 2: ((2-(Difluoromethyl)-4,5-difluorophenyl)ethynyl)trimethylsilane (Int 26c)

To a solution of 4,5-difluoro-2-((trimethylsilyl)ethynyl)benzaldehyde (Int 26b) (1.67 g, 7.00 mmol) in DCM (10 mL) was added DAST (2.25 g, 14.00 mmol) at 0° C. and the mixture was stirred at rt for 4 h. The mixture was poured into ice-water and extracted with DCM (2×30 mL). The combined organic layers were dried over anhydrous MgSO$_4$, filtered and concentrated to dryness. The residue was purified by column chromatography (gradient 5-30% EtOAc in PE) to give the title compound as a yellow oil.

Step 3: 1-(Difluoromethyl)-2-ethynyl-4,5-difluorobenzene (Int 26d)

To a solution of ((2-(difluoromethyl)-4,5-difluorophenyl)ethynyl)trimethylsilane (Int 26c) (1.30 g, 5.00 mmol) in MeOH (2 mL) was added K$_2$CO$_3$ (1.38 g, 10.00 mmol) and the mixture was stirred at rt for 0.5 h. The mixture was poured into ice-water and extracted with diethyl ether (2×10 mL). The combined organic layers were dried over anhydrous MgSO$_4$, filtered and concentrated to dryness to give the title compound.

Steps 4-5: tert-Butyl 6-chloro-2-(2-(difluoromethyl)-4,5-difluorophenyl)-1H-pyrrolo[3,2-c]pyridine-1-carboxylate (Int 26)

The title compound was prepared similar as described for Intermediate 2 steps 3 and 4 using in step 3 1-(difluoromethyl)-2-ethynyl-4,5-difluorobenzene (Int 26d) in place of 1-ethynyl-2-methylbenzene.

Example 1: 1-Methyl-N-(2-(o-tolyl)-1H-pyrrolo[3,2-c]pyridin-6-yl)-1H-pyrazole-5-carboxamide (1)

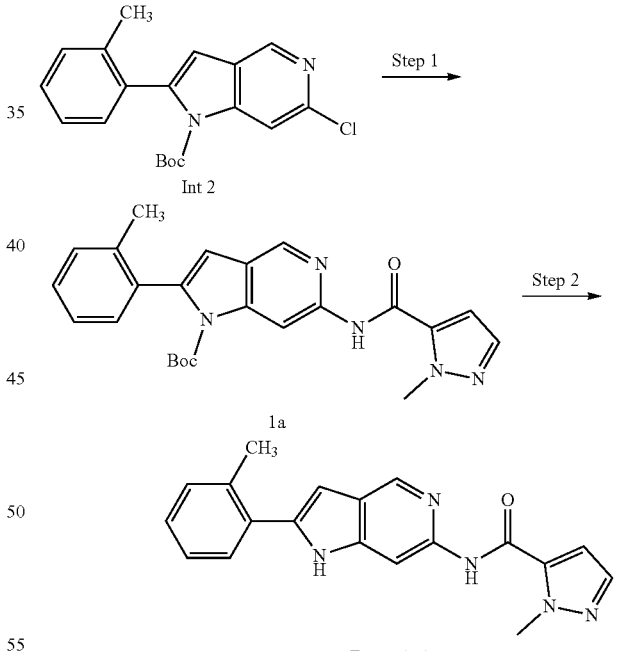

Example 1

Step 1: tert-Butyl 6-(1-methyl-1H-pyrazole-5-carboxamido)-2-(o-tolyl)-1H-pyrrolo[3,2-c]pyridine-1-carboxylate (1a)

Pd$_2$(dba)$_3$ (230 mg, 0.25 mmol) was added to a mixture of tert-butyl 6-chloro-2-(o-tolyl)-1H-pyrrolo[3,2-c]pyridine-1-carboxylate (Int 2) (170 mg, 0.5 mmol), potassium phosphate (347 mg, 1.64 mmol), 1-methyl-1H-pyrazole-5-carboxamide (125 mg, 1.00 mmol) and tBuXPhos (150 mg, 0.35 mmol) in t-BuOH (6.0 mL) and water (0.2 mL). The mixture was heated at 90° C. for 5 h under microwave irradiation. The mixture was filtered and the residue washed with DCM (20 mL). The filtrate was concentrated to dryness and the residue was purified by column chromatography (gradient 5-100% EtOAc in PE) to give the title compound as a yellow solid.

Step 2: 1-Methyl-N-(2-(o-tolyl)-1H-pyrrolo[3,2-c]pyridin-6-yl)-1H-pyrazole-5-carboxamide (1)

To a mixture of tert-butyl 6-(1-methyl-1H-pyrazole-5-carboxamido)-2-(o-tolyl)-1H-pyrrolo[3,2-c]pyridine-1-carboxylate (1a) (164 mg, 0.38 mmol) in DCM (8 mL) was added TFA (1 mL) and the mixture was stirred at rt overnight. The mixture was purified by reverse phase chromatography (c18, acetonitrile 25-55%/(10 mM aqueous NH$_4$HCO$_3$) to give the title compound as a white solid. $^1$H NMR (400 MHz, CDCl$_3$): δ ppm 8.63 (s, 1H), 8.61-8.52 (m, 2H), 8.39 (s, 1H), 7.52 (d, J=2.4 Hz, 1H), 7.46 (d, J=6.8 Hz, 1H), 7.35-7.27 (m, 3H), 6.76 (d, J=2.0 Hz, 1H), 6.64 (s, 1H), 4.23 (s, 3H), 2.49 (s, 3H). (ESI): m/z 332.2 [M+H]$^+$.

Example 1/1: 1-Methyl-N-(2-(2-(trifluoromethyl)phenyl)-1H-pyrrolo[3,2-c]pyridin-6-yl)-1H-pyrazole-5-carboxamide (1/1)

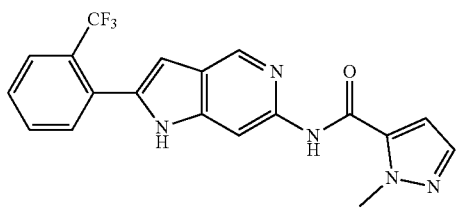 [SMILES: Cn1nccc1C(=O)Nc1cc2[nH]c(-c3ccccc3C(F)(F)F)cc2cn1]

The title compound was prepared similar as described for Example 1 using in step 1 tert-butyl 6-chloro-2-(2-(trifluoromethyl)phenyl)-1H-pyrrolo[3,2-c]pyridine-1-carboxylate (Int 2/1) in place of tert-butyl 6-chloro-2-(o-tolyl)-1H-pyrrolo[3,2-c]pyridine-1-carboxylate (Int 2). $^1$H NMR (500 MHz, DMSO-d$_6$): δ ppm 12.71 (s, 1H), 11.34 (s, 1H), 8.97 (s, 1H), 8.02 (s, 1H), 7.97 (d, J=7.5 Hz, 1H), 7.89-7.86 (m, 1H), 7.78-7.75 (m, 2H), 7.62 (d, J=2.1 Hz, 1H), 7.27 (d, J=2.1 Hz, 1H), 6.96 (s, 1H), 4.17 (s, 3H). (ESI): m/z 385.9 [M+H]$^+$.

Example 1/2: 1-Methyl-N-(2-(2-(trifluoromethyl)phenyl)-1H-pyrrolo[3,2-c]pyridin-6-yl)-1H-1,2,4-triazole-5-carboxamide (1/2)

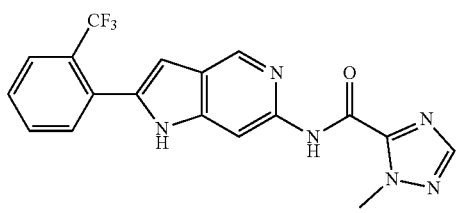 [SMILES: Cn1ncnc1C(=O)Nc1cc2[nH]c(-c3ccccc3C(F)(F)F)cc2cn1]

The title compound was prepared similar as described for Example 1 using in step 1 tert-butyl 6-chloro-2-(2-(trifluoromethyl)phenyl)-1H-pyrrolo[3,2-c]pyridine-1-carboxylate (Int 2/1) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.57 (s, 1H), 11.02 (s, 1H), 8.93 (s, 1H), 8.25 (s, 1H), 8.19 (s, 1H), 7.96 (d, J=8.0 Hz, 1H), 7.88-7.85 (m, 1H), 7.77-7.74 (m, 2H), 6.92 (s, 1H), 4.25 (s, 3H). (ESI): m/z 386.9 [M+H]$^+$.

Example 1/3: N-(2-(2-(Trifluoromethyl)phenyl)-1H-pyrrolo[3,2-c]pyridin-6-yl) picolinamide (1/3)

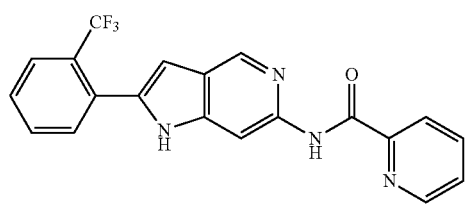 [SMILES: O=C(Nc1cc2[nH]c(-c3ccccc3C(F)(F)F)cc2cn1)c1ccccn1]

The title compound was prepared similar as described for Example 1 using in step 1 tert-butyl 6-chloro-2-(2-(trifluoromethyl)phenyl)-1H-pyrrolo[3,2-c]pyridine-1-carboxylate (Int 2/1) in place of tert-butyl 6-chloro-2-(o-tolyl)-1H-pyrrolo[3,2-c]pyridine-1-carboxylate (Int 2) and picolinamide in place of 1-methyl-1H-pyrazole-5-carboxamide. $^1$H NMR (500 MHz, DMSO-d$_6$): δ ppm 12.55 (s, 1H), 11.26 (s, 1H), 8.94 (s, 1H), 8.82 (d, J=4.1 Hz, 1H), 8.37 (s, 1H), 8.27 (d, J=7.8 Hz, 1H), 8.17-8.14 (m, 1H), 7.96 (d, J=7.9 Hz, 1H), 7.87-7.86 (m, 1H), 7.79-7.74 (m, 3H). (ESI): 382.9 m/z [M+H]$^+$.

Example 1/4: N-(2-(5-Fluoro-2-(trifluoromethyl)phenyl)-1H-pyrrolo[3,2-c]pyridin-6-yl)-1-methyl-1H-1,2,4-triazole-5-carboxamide (1/4)

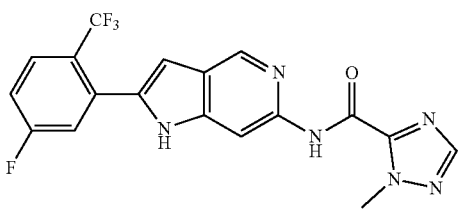 [SMILES: Cn1ncnc1C(=O)Nc1cc2[nH]c(-c3cc(F)ccc3C(F)(F)F)cc2cn1]

The title compound was prepared similar as described for Example 1 using in step 1 tert-butyl 6-chloro-2-(5-fluoro-2-(trifluoromethyl)phenyl)-1H-pyrrolo[3,2-c]pyridine-1-carboxylate (Int 2/2) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 12.57 (s, 1H), 10.95 (s, 1H), 8.94 (s, 1H), 8.24 (s, 1H), 8.20 (s, 1H), 8.05-8.03 (m, 1H), 7.72-7.70 (m, 1H), 7.63-7.59 (m, 1H), 6.96 (s, 1H), 4.24 (s, 3H). (ESI): 405.1 m/z [M+H]$^+$.

Example 1/5: N-(2-(2-(Difluoromethyl)phenyl)-1H-pyrrolo[3,2-c]pyridin-6-yl)-4-methyl-4H-1,2,4-triazole-3-carboxamide (1/5)

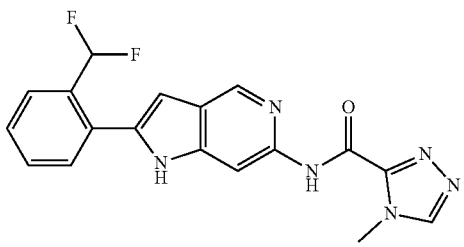 [SMILES: Cn1cnnc1C(=O)Nc1cc2[nH]c(-c3ccccc3C(F)F)cc2cn1]

The title compound was prepared similar as described for Example 1 using in step 1 tert-butyl 6-chloro-2-(2-(difluoromethyl)phenyl)-1H-pyrrolo[3,2-c]pyridine-1-carboxylate (Int 2/2) in place of tert-butyl 6-chloro-2-(o-tolyl)-1H-pyrrolo[3,2-c]pyridine-1-carboxylate (Int 2) and 4-methyl-4H-1,2,4-triazole-3-carboxamide (Int 4) in place of 1-methyl-1H-pyrazole-5-carboxamide. $^1$H NMR (500 MHz, DMSO-$d_6$): δ ppm 12.69 (s, 1H), 11.42 (s, 1H), 8.98 (s, 1H), 8.83 (s, 1H), 8.16 (s, 1H), 7.87-7.85 (m, 1H), 7.76-7.75 (m, 2H), 7.70-7.67 (m, 1H), 7.15 (t, J=54.5 Hz, 1H), 6.96 (s, 1H), 3.99 (s, 3H). (ESI): 369.1 m/z [M+H]$^+$.

Example 1/6: N-(2-(2-(Difluoromethyl)phenyl)-1H-pyrrolo[3,2-c]pyridin-6-yl)-1-methyl-1H-1,2,4-triazole-5-carboxamide (1/6)

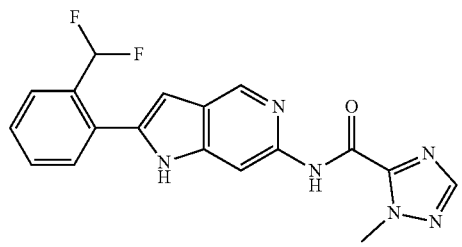 [SMILES: Cn1ncnc1C(=O)Nc1cc2[nH]c(-c3ccccc3C(F)F)cc2cn1]

The title compound was prepared similar as described for Example 1 using in step 1 tert-butyl 6-chloro-2-(2-(difluoromethyl)phenyl)-1H-pyrrolo[3,2-c]pyridine-1-carboxylate (Int 2/4) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-$d_6$): δ ppm 12.58 (s, 1H), 10.97 (s, 1H), 8.93 (s, 1H), 8.24 (s, 1H), 8.21 (s, 1H), 7.86-7.85 (m, 1H), 7.76-7.75 (m, 2H), 7.69-7.66 (m, 1H), 7.15 (t, J=54.5 Hz, 1H), 6.91 (s, 1H), 4.25 (s, 3H). (ESI): 369.1 m/z [M+H]$^+$.

Example 1/7: N-(2-(5-Fluoro-2-(trifluoromethyl)phenyl)-1H-pyrrolo[3,2-c]pyridin-6-yl)-4-methyl-4H-1,2,4-triazole-3-carboxamide (Int 1/7)

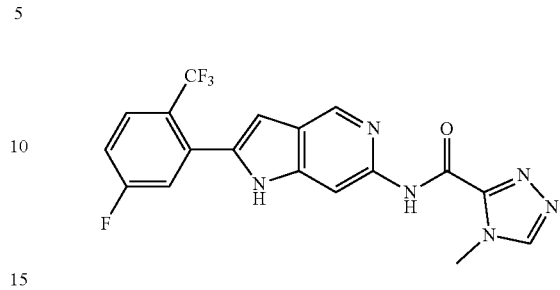

The title compound was prepared similar as described for Example 1 using in step 1 tert-butyl 6-chloro-2-(5-fluoro-2-(trifluoromethyl)phenyl)-1H-pyrrolo[3,2-c]pyridine-1-carboxylate (Int 2/1) in place of tert-butyl 6-chloro-2-(o-tolyl)-1H-pyrrolo[3,2-c]pyridine-1-carboxylate (Int 2) and 4-methyl-4H-1,2,4-triazole-3-carboxamide (Int 4) in place of 1-methyl-1H-pyrazole-5-carboxamide. $^1$H NMR (400 MHz, DMSO-$d_6$): δ ppm 12.67 (s, 1H), 11.31 (s, 1H), 8.97 (s, 1H), 8.83 (s, 1H), 8.16 (s, 1H), 8.06-8.03 (m, 1H), 7.72-7.71 (m, 1H), 7.63-7.60 (s, 1H), 7.0 (s, 1H), 3.99 (s, 3H). (ESI): 405.1 m/z [M+H]$^+$.

NMR analytical samples of Examples 1/1 to 1/7 may contain residual TFA.

Example 1/8: N-(2-(2-(Difluoromethyl)-5-fluorophenyl)-1H-pyrrolo[3,2-c]pyridin-6-yl)-1-methyl-1H-1,2,4-triazole-5-carboxamide (1/8)

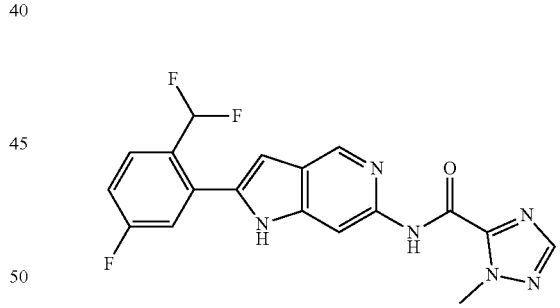

The title compound was prepared similar as described for Example 1 using in step 1 tert-butyl 6-chloro-2-(2-(difluoromethyl)-5-fluorophenyl)-1H-pyrrolo[3,2-c]pyridine-1-carboxylate (Int 2/3) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (DMSO-$d_6$, 400 MHz): δ ppm 12.07 (s, 1H), 9.98 (s, 1H), 8.75 (s, 1H), 8.25 (s, 1H), 8.17 (s, 1H), 7.91-7.88 (m, 1H), 7.61-7.58 (m, 1H), 7.50-7.46 (m, 1H), 7.15 (t, J=54.2 Hz, 1H), 6.80 (s, 1H), 4.24 (s, 3H). (ESI): 387.0 m/z [M+H]$^+$.

Example 1/9: N-(2-(2-(Difluoromethyl)furan-3-yl)-1H-pyrrolo[3,2-c]pyridin-6-yl)-1-methyl-1H-1,2,4-triazole-5-carboxamide (1/9)

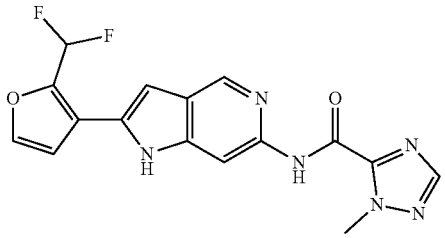 [SMILES: Cn1ncnc1C(=O)Nc1cc2[nH]c(-c3ccoc3C(F)F)cc2cn1]

The title compound was prepared similar as described for Example 1 using in step 1 tert-butyl 6-chloro-2-(2-(difluoromethyl)furan-3-yl)-1H-pyrrolo[3,2-c]pyridine-1-carboxylate (Int 6) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (500 MHz, DMSO-d$_6$): δ ppm 11.96 (s, 1H), 9.96 (s, 1H), 8.68 (s, 1H), 8.25 (s, 1H), 8.17 (s, 1H), 8.03 (s, 1H), 7.38 (t, J=51.5 Hz, 1H), 7.08 (s, 1H), 6.85 (s, 1H), 4.23 (s, 3H). (ESI): m/z 359.1 [M+H]$^+$.

Example 1/10: N-(2-(2,5-Bis(trifluoromethyl)phenyl)-1H-pyrrolo[3,2-c]pyridin-6-yl)-1-methyl-1H-1,2,4-triazole-5-carboxamide (1/10)

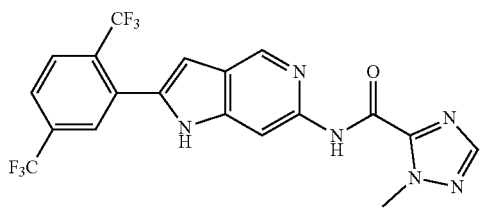 [SMILES: Cn1ncnc1C(=O)Nc1cc2[nH]c(-c3cc(C(F)(F)F)ccc3C(F)(F)F)cc2cn1]

The title compound was prepared similar as described for Example 1 using in step 1 tert-butyl 2-(2,5-bis(trifluoromethyl)phenyl)-6-chloro-1H-pyrrolo[3,2-c]pyridine-1-carboxylate (Int 2/5) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d$_6$): δ ppm 12.11 (s, 1H), 9.99 (s, 1H), 8.74 (s, 1H), 8.24 (s, 1H), 8.20-8.18 (m, 2H), 8.12-8.08 (m, 2H), 6.83 (s, 1H), 4.23 (s, 3H). (ESI): m/z 455.0 [M+H]$^+$.

Example 1/11: N-(2-(5-Cyclopropyl-2-(trifluoromethyl)phenyl)-1H-pyrrolo[3,2-c]pyridin-6-yl)-1-methyl-1H-1,2,4-triazole-5-carboxamide (1/11)

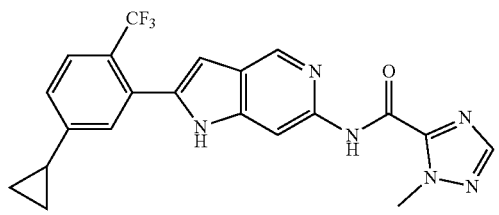 [SMILES: Cn1ncnc1C(=O)Nc1cc2[nH]c(-c3cc(C4CC4)ccc3C(F)(F)F)cc2cn1]

The title compound was prepared similar as described for Example 1 using in step 1 tert-butyl 6-chloro-2-(5-cyclopropyl-2-(trifluoromethyl)phenyl)-1H-pyrrolo[3,2-c]pyridine-1-carboxylate (Int 25) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d$_6$): δ ppm 11.93 (s, 1H), 9.96 (s, 1H), 8.69 (s, 1H), 8.22 (s, 1H), 8.18 (s, 1H), 7.76 (d, J=8.0 Hz, 1H), 7.40-7.53 (m, 2H), 6.70 (s, 1H), 4.23 (s, 3H), 2.12-2.08 (m, 1H), 1.11-1.06 (m, 2H), 0.89-0.85 (m, 2H). (ESI): m/z 427.0 [M+H]$^+$.

Example 1/12: N-(2-(2-(Difluoromethyl)-4,5-difluorophenyl)-1H-pyrrolo[3,2-c]pyridin-6-yl)-1-methyl-1H-1,2,4-triazole-5-carboxamide (1/12)

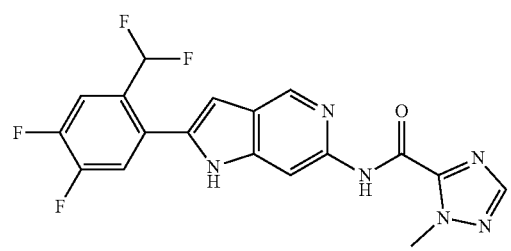 [SMILES: Cn1ncnc1C(=O)Nc1cc2[nH]c(-c3cc(F)c(F)cc3C(F)F)cc2cn1]

The title compound was prepared similar as described for Example 1 using in step 1 tert-butyl 6-chloro-2-(2-(difluoromethyl)-4,5-difluorophenyl)-1H-pyrrolo[3,2-c]pyridine-1-carboxylate (Int 26) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d$_6$): δ ppm 12.08 (s, 1H), 9.99 (s, 1H), 8.75 (s, 1H), 8.24 (s, 1H), 8.18 (s, 1H), 7.95-7.84 (m, 2H), 7.14 (t, J=53.8 Hz, 1H), 6.77 (s, 1H), 4.23 (s, 3H). (ESI): m/z 405.1 [M+H]$^+$.

Example 1/13: N-(2-(5-Ethyl-2-(trifluoromethyl)phenyl)-1H-pyrrolo[3,2-c]pyridin-6-yl)-1-methyl-1H-1,2,4-triazole-5-carboxamide (1/13)

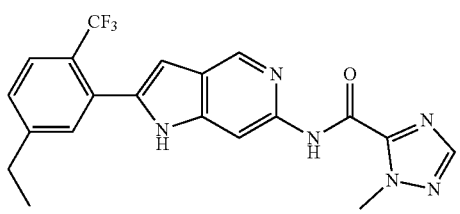 [SMILES: CCc1ccc(C(F)(F)F)c(-c2cc3cnc(NC(=O)c4ncnn4C)cc3[nH]2)c1]

The title compound was prepared similar as described for Example 1 using in step 1 tert-butyl 6-chloro-2-(5-ethyl-2-(trifluoromethyl)phenyl)-1H-pyrrolo[3,2-c]pyridine-1-carboxylate (Int 25/1) in place of tert-butyl 6-chloro-2-(o-tolyl)-1H-pyrrolo[3,2-c]pyridine-1-carboxylate (Int 2) and 1-methyl-1H-1,2,4-triazole-5-carboxamide (Int 3) in place of 1-methyl-1H-pyrazole-5-carboxamide. $^1$H NMR (400 MHz, DMSO-d$_6$): δ ppm 11.92 (s, 1H), 9.91 (br s, 1H), 8.67 (s, 1H), 8.20 (s, 1H), 8.15 (s, 1H), 7.80 (d, J=8.0 Hz, 1H), 7.56 (s, 1H), 7.51 (d, J=8.4 Hz, 1H), 6.68 (s, 1H), 4.21 (s, 3H), 2.74 (q, J=7.6 Hz, 2H), 1.23 (t, J=7.6 Hz, 3H). (ESI): m/z 415.3 [M+H]+.

Example 2: N-(2-(2-Isopropylphenyl)-1H-pyrrolo[3,2-c]pyridin-6-yl)-1-methyl-1H-1,2,4-triazole-5-carboxamide (2)

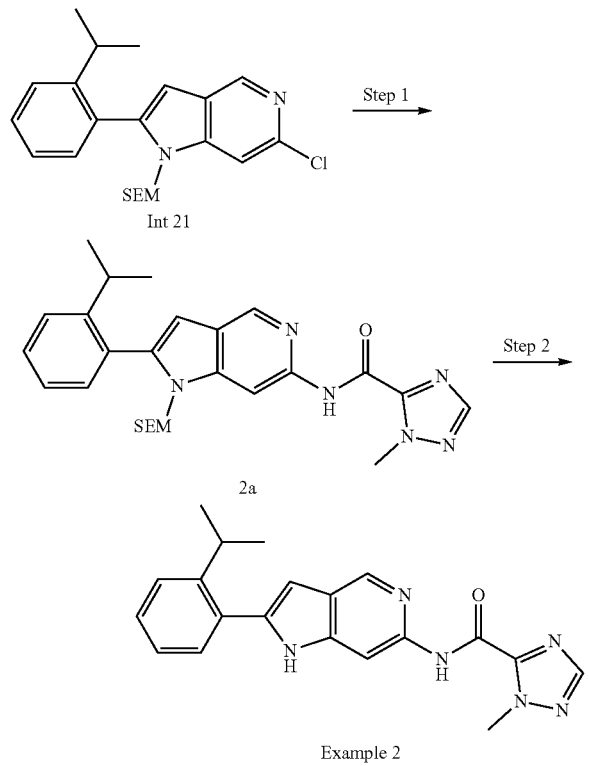

Step 1: N-(2-(2-Isopropylphenyl)-1-((2-(trimethylsilyl)ethoxy)methyl)-1H-pyrrolo[3,2-c]pyridin-6-yl)-1-methyl-1H-1,2,4-triazole-5-carboxamide (2a)

A solution of 6-chloro-2-(2-isopropylphenyl)-1-((2-(trimethylsilyl)ethoxy)methyl)-1H-pyrrolo[3,2-c]pyridine (Int 21) (130 mg, 0.33 mmol), 1-methyl-1H-1,2,4-triazole-5-carboxamide (Int 3) (84 mg, 0.67 mmol), Pd₂(dba)₃ (30 mg, 0.03 mmol), tBuXPhos (14 mg, 0.03 mmol) and K₂CO₃ (182 mg, 1.3 mmol) in t-BuOH/H₂O (9 mL/0.3 mL) was stirred at 120° C. overnight in a sealed tube. The mixture was diluted with saturated aqueous NH₄Cl solution. The mixture was extracted with DCM (2×55 mL). The combined organic layers were washed with brine, dried over Na₂SO₄, filtered and concentrated to dryness. The residue was purified by preparative TLC (PE/EtOAc=3:1) to give the title compound as a yellow solid.

Step 2: N-(2-(2-Isopropylphenyl)-1H-pyrrolo[3,2-c]pyridin-6-yl)-1-methyl-1H-1,2,4-triazole-5-carboxamide (2)

A solution of N-(2-(2-isopropylphenyl)-1-((2-(trimethylsilyl)ethoxy)methyl)-1H-pyrrolo[3,2-c]pyridin-6-yl)-1-methyl-1H-1,2,4-triazole-5-carboxamide (2a) (70 mg, 0.14 mmol) in DCM/TFA (5 mL/5 mL) was stirred at 50° C. for 2 h. The mixture was concentrated to dryness and the residue was dissolved in acetonitrile/H₂O (5 mL/1 mL). K₂CO₃ (200 mg, 1.44 mmol) was added and the mixture was stirred for 1 h at the same temperature. The mixture was extracted with DCM (2×45 mL). The combined organic layers were washed with brine, dried over Na₂SO₄, filtered and concentrated to dryness. The residue was purified by preparative TLC (PE/EtOAc=2:1) to give the title compound as a white solid. ¹H NMR (CD₃OD, 400 MHz): δ ppm 8.60 (s, 1H), 8.32 (s, 1H), 8.01 (s, 1H), 7.48 (d, J=8.0 Hz, 1H), 7.43-7.39 (m, 2H), 7.27 (t, J=7.2 Hz, 1H), 6.57 (s, 1H), 4.31 (s, 3H), 3.34-3.31 (m, 1H), 1.23 (d, J=6.8 Hz, 6H). (ESI): m/z 361.0 [M+H]+.

Examples 2/1 to 2/7

The following Examples were prepared similar as described for Example 2 using the appropriate carboxamide building blocks and intermediates.

| # | Building blocks | Structure | Analytical data |
|---|---|---|---|
| 2/1 | Int 21/2 Int 3 | (2-methylphenyl pyrrolopyridine triazole carboxamide) | ¹H NMR (CD₃OD, 300 MHz): δ ppm 8.60 (s, 1H), 8.34 (s, 1H), 8.00 (s, 1H), 7.53-7.52 (m, 1H), 7.36-7.30 (m, 3H), 6.68 (s, 1H), 4.30 (s, 3H), 2.47 (s, 3H). (ESI): m/z 333.0 [M + H]+. |
| 2/2 | Int 21/1 Int 3 | (2,6-dichlorophenyl pyrrolopyridine triazole carboxamide) | ¹H NMR (CD₃OD, 400 MHz): δ ppm 8.65 (s, 1H), 8.32 (s, 1H), 8.01 (s, 1H), 7.55 (d, J = 8.0 Hz, 2H), 7.44 (t, J = 7.6 Hz, 1H), 6.66 (s, 1H), 4.31 (s, 3H). (ESI): m/z 386.9 [M + H]+. |

| # | Building blocks | Structure | Analytical data |
|---|---|---|---|
| 2/3 | Int 22 Int 3 | 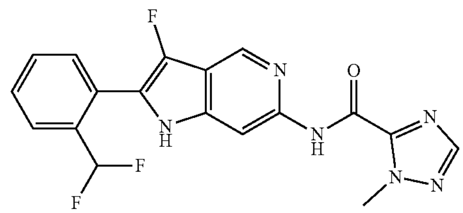 [SMILES: Cn1ncnc1C(=O)Nc1cc2[nH]c(-c3ccccc3C(F)F)c(F)c2cn1] | $^1$H NMR (CD$_3$OD, 400 MHz): δ ppm 8.68 (s, 1H), 8.33 (s, 1H), 8.01 (s, 1H), 7.84-7.82 (m, 1H), 7.68-7.59 (m, 3H), 6.87 (t, J = 54.8 Hz, 1H), 4.31 (s, 3H). (ESI): m/z 387.2 [M + H]$^+$. |
| 2/4 | Int 23 Int 3 | 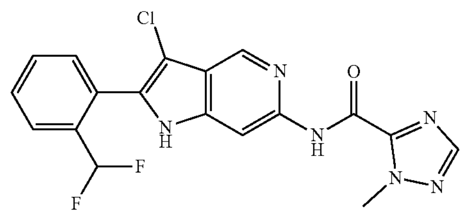 [SMILES: Cn1ncnc1C(=O)Nc1cc2[nH]c(-c3ccccc3C(F)F)c(Cl)c2cn1] | $^1$H NMR (CD$_3$OD, 400 MHz): δ ppm 8.64 (s, 1H), 8.36 (s, 1H), 8.01 (s, 1H), 7.85-7.82 (m, 1H), 7.70-7.67 (m, 2H), 7.58-7.56 (m, 1H), 6.74 (t, J = 54.8 Hz, 1H), 4.31 (s, 3H). (ESI): m/z 402.9 [M + H]$^+$. |
| 2/5 | Int 20/1 Int 3 | 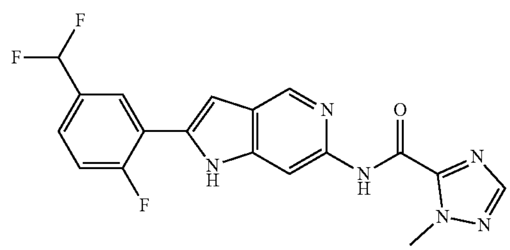 [SMILES: Cn1ncnc1C(=O)Nc1cc2[nH]c(-c3cc(C(F)F)ccc3F)cc2cn1] | $^1$H NMR (DMSO-d$_6$, 400 MHz): δ ppm 12.16 (s, 1H), 9.97 (s, 1H), 8.72 (s, 1H), 8.28 (s, 1H), 8.17-8.16 (m, 2H), 7.65-7.63 (m, 1H), 7.58-7.55 (m, 1H), 7.28-7.00 (m, 2H), 4.24 (s, 3H). (ESI): m/z 387.0 [M + H]$^+$. |
| 2/6 | Int 20/2 Int 3 | 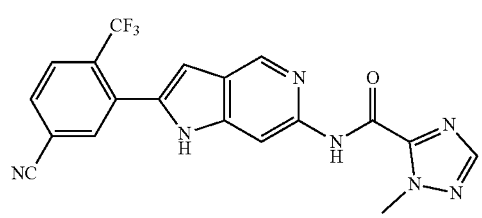 [SMILES: Cn1ncnc1C(=O)Nc1cc2[nH]c(-c3cc(C#N)ccc3C(F)(F)F)cc2cn1] | $^1$H NMR (400 MHz, CD$_3$OD): δ ppm 8.67 (s, 1H), 8.36 (s, 1H), 8.08-8.05 (m, 2H), 8.02-8.01 (m, 2H), 6.81 (s, 1H), 4.31 (s, 3H). (ESI): m/z 412.1 [M + H]$^+$. |
| 2/7 | Int 20 Int 3 (Step 2 TBAF deprotection) | 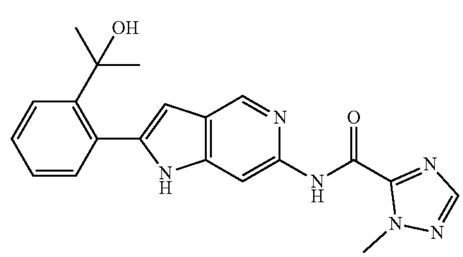 [SMILES: Cn1ncnc1C(=O)Nc1cc2[nH]c(-c3ccccc3C(C)(C)O)cc2cn1] | $^1$H NMR (CD$_3$OD, 400 MHz): δ ppm 8.60 (s, 1H), 8.30 (s, 1H), 8.00 (s, 1H), 7.76 (d, J = 8.0 Hz, 1H), 7.48 (d, J = 8.0 Hz, 1H), 7.42 (t, J = 8 Hz, 1H), 7.33 (t, J = 8 Hz, 1H), 6.65 (s, 1H), 4.31 (s, 3H), 1.45 (s, 6H). (ESI): m/z 377.3 [M + H]$^+$. |

Example 3: N-(2-(2-(Difluoromethyl)-5-fluorophenyl)-1H-pyrrolo[3,2-c]pyridin-6-yl)-N,1-dimethyl-1H-1,2,4-triazole-5-carboxamide (3)

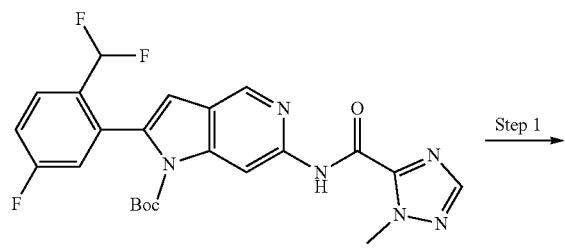

Example 1/5, Step 1

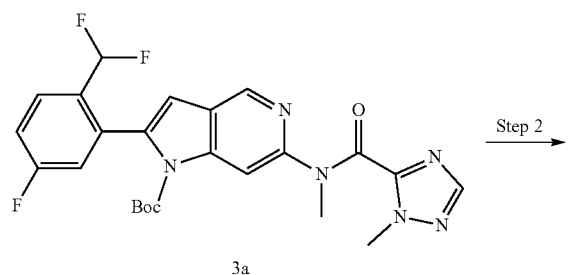

3a

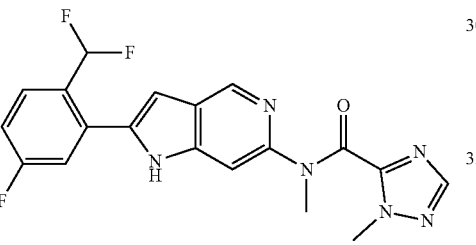

Example 3

Step 1: tert-Butyl 2-(2-(difluoromethyl)-5-fluorophenyl)-6-(N, 1-dimethyl-1H-1,2,4-triazole-5-carboxamide)-1H-pyrrolo[3,2-c]pyridine-1-carboxylate (3a)

A mixture of tert-butyl 2-(2-(difluoromethyl)-5-fluorophenyl)-6-(1-methyl-1H-1,2,4-triazole-5-carboxamido)-1H-pyrrolo[3,2-c]pyridine-1-carboxylate (Example 1/5, Step 1) (300 mg, 0.64 mmol), $Cs_2CO_3$ (313 mg, 0.96 mmol) and MeI (109 mg, 0.77 mmol) in DMF (10 mL) was stirred at rt overnight. The mixture was concentrated to dryness and the residue was purified by prep-HPLC to give the title compound as a white solid.

Step 2: N-(2-(2-(Difluoromethyl)-5-fluorophenyl)-1H-pyrrolo[3,2-c]pyridin-6-yl)-N,1-dimethyl-1H-1,2,4-triazole-5-carboxamide (3)

To a mixture of tert-butyl 2-(2-(difluoromethyl)-5-fluorophenyl)-6-(N,1-dimethyl-1H-1,2,4-triazole-5-carboxamido)-1H-pyrrolo[3,2-c]pyridine-1-carboxylate (3a) (250 mg, 0.52 mmol) in DCM (5 mL) was added TFA (2.5 mL) and the mixture was stirred at rt overnight. The mixture was concentrated to dryness and the residue was purified by prep-HPLC to give the title compound as a white solid. $^1$H NMR (500 MHz, DMSO-$d_6$): δ ppm 12.54 (s, 1H), 8.80 (s, 1H), 7.91-7.88 (m, 1H), 7.73 (s, 1H), 7.63-7.48 (m, 3H), 7.13 (t, J=54.5 Hz, 1H), 6.89 (s, 1H), 4.02 (s, 3H), 3.53 (s, 3H). (ESI): m/z 401.1 [M+H]$^+$.

Example 4: N-(2-(2-(Difluoromethyl)phenyl)-1H-pyrrolo[3,2-c]pyridin-6-yl)-5-methylthiazole-4-carboxamide (4)

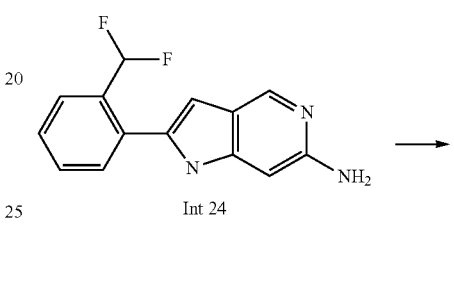

Int 24

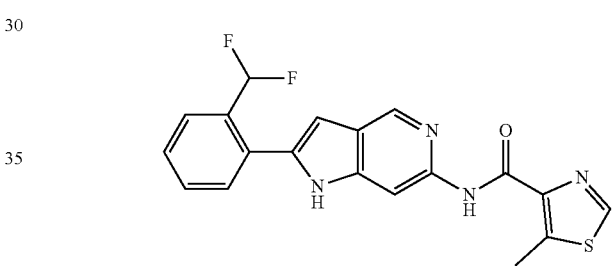

Example 4

A solution of 2-(2-(difluoromethyl)phenyl)-1H-pyrrolo[3,2-c]pyridin-6-amine (Int 24) (25 mg, 0.10 mmol), 5-methylthiazole-4-carboxylic acid (28 mg, 0.19 mmol), HATU (42 mg, 0.10 mmol) and Et$_3$N (24 mg, 0.24 mmol) in DMF (10 mL) was stirred at rt overnight. The mixture was diluted with water (100 mL) and extracted with DCM (2×45 mL). The combined organic layers were washed with brine, dried over Na$_2$SO$_4$, filtered and concentrated to dryness. The residue was purified by prep-HPLC to give the title compound as a white solid. $^1$H NMR (MeOD, 400 MHz): δ ppm 8.82 (s, 1H), 8.66 (s, 1H), 8.34 (s, 1H), 7.84 (d, J=7.6 Hz, 1H) 7.70-7.60 (m, 3H), 6.93 (t, J=54.8 Hz, 1H), 6.77 (s, 1H), 2.91 (s, 3H). (ESI): 384.9 m/z [M+H]$^+$.

Examples 4/1 to 4/3

The following Examples were prepared similar as described for Example 4 using the appropriate carboxamide building blocks and intermediates.

| # | Building blocks | Structure | Analytical data |
|---|---|---|---|
| 4/1 | Int 24, 1-methyl-1H-imidazole-5-carboxylic acid | 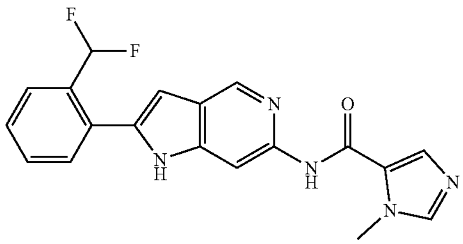 [SMILES: Cn1cncc1C(=O)Nc1cc2[nH]c(-c3ccccc3C(F)F)cc2cn1] | $^1$H NMR (MeOD, 400 MHz): δ ppm 8.65 (s, 1H), 8.18 (s, 1H), 7.84-7.82 (m, 3H), 7.70-7.58 (m, 3H) 6.92 (t, J = 54.8 Hz, 1H), 6.71 (s, 1H), 4.01 (s, 3H). (ESI): m/z 368.0 [M + H]$^+$. |
| 4/2 | Int 24, 1-methyl-1H-imidazole-2-carboxylic acid | 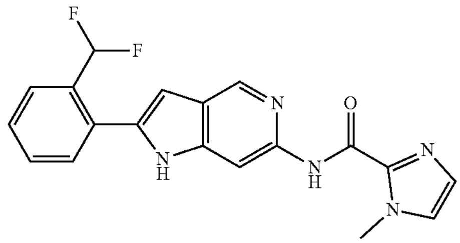 [SMILES: Cn1ccnc1C(=O)Nc1cc2[nH]c(-c3ccccc3C(F)F)cc2cn1] | $^1$H NMR (MeOD, 400 MHz): δ ppm 8.63 (s, 1H), 8.33 (s, 1H), 7.83 (d, J = 7.6 Hz, 1H) 7.70-7.58 (m, 3H), 7.30 (s, 1H), 7.10 (s, 1H) 6.92 (t, J = 54.8 Hz, 1H), 6.71 (s, 1H), 4.12 (s, 3H). (ESI): m/z 368.2 [M + H]$^+$. |
| 4/3 | Int 24, 5-methyloxazole-4-carboxylic acid | 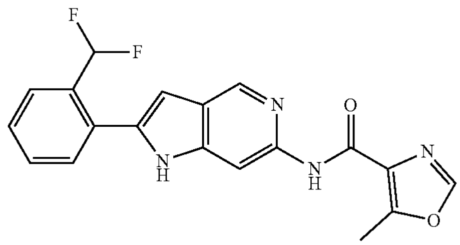 [SMILES: Cc1ocnc1C(=O)Nc1cc2[nH]c(-c3ccccc3C(F)F)cc2cn1] | $^1$H NMR (MeOD, 400 MHz): δ ppm 8.63 (s, 1H), 8.36 (s, 1H), 8.10 (s, 1H), 7.83 (d, J = 7.6 Hz, 1H) 7.70-7.58 (m, 3H), 6.92 (t, J = 54.8 Hz, 1H), 6.72 (s, 1H), 2.71 (s, 3H). (ESI): m/z 369.0 [M + H]$^+$. |

Example 5: N-(3-Cyano-2-(2-(difluoromethyl)phenyl)-1H-pyrrolo[3,2-c]pyridin-6-yl)-1-methyl-1H-1,2,4-triazole-5-carboxamide (5)

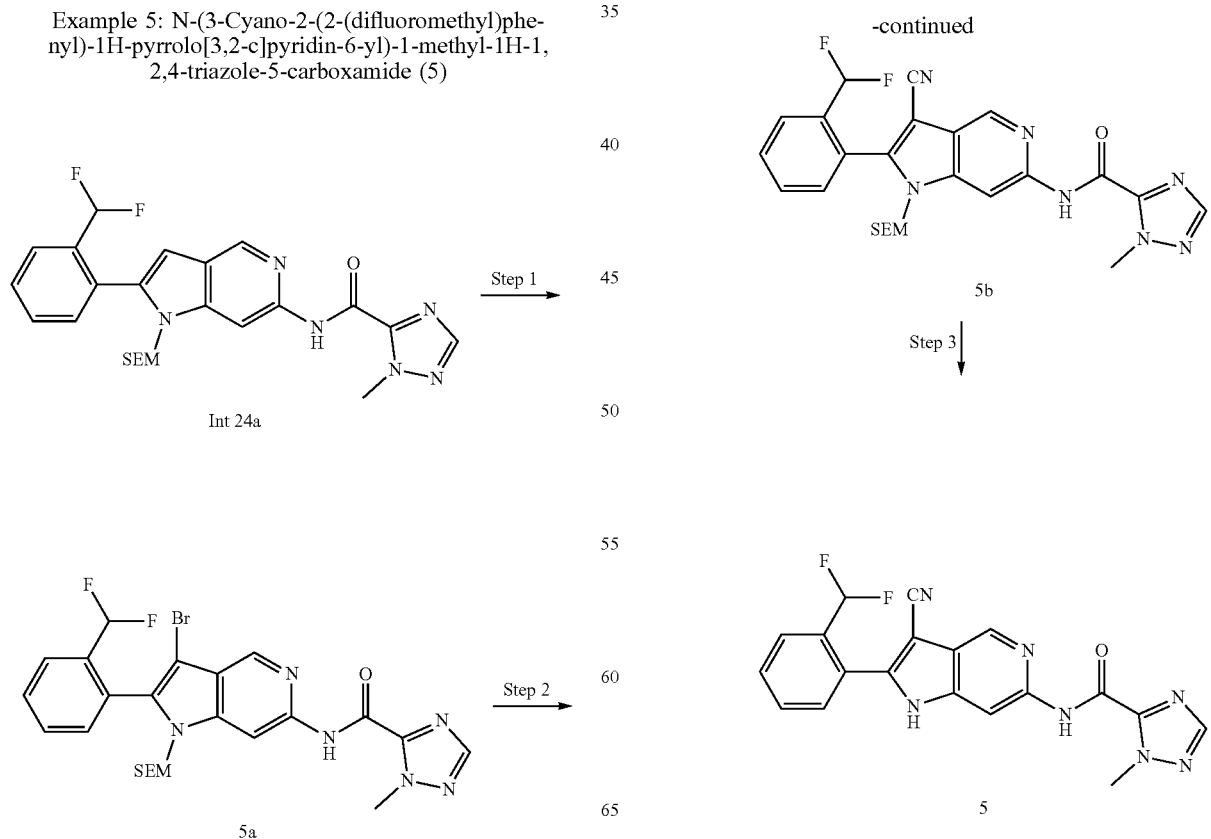

Step 1: N-(3-Bromo-2-(2-(difluoromethyl)phenyl)-1-((2-(trimethylsilyl)ethoxy) methyl)-1H-pyrrolo[3,2-c]pyridin-6-yl)-1-methyl-1H-1,2,4-triazole-5-carboxamide (5a)

To a solution of N-(2-(2-(difluoromethyl)phenyl)-1-((2-(trimethylsilyl)ethoxy)methyl)-1H-pyrrolo[3,2-c]pyridin-6-yl)-1-methyl-1H-1,2,4-triazole-5-carboxamide (Int 24a) (440 mg, 0.88 mmol) in DMF (15 mL) was added NBS (158 mg, 0.88 mmol) at −60° C. to −55° C. and the mixture was stirred for 2 h at the same temperature. The mixture was diluted with water (30 ml) and extracted with EtOAc (3×10 mL). The combined organic layers were dried over anhydrous $Na_2SO_4$, filtered and concentrated to dryness. The residue was purified by silica gel chromatography (PE/EtOAc=6:1) to give the title compound.

Step 2: N-(3-Cyano-2-(2-(difluoromethyl)phenyl)-1-((2-(trimethylsilyl)ethoxy) methyl)-1H-pyrrolo[3,2-c]pyridin-6-yl)-1-methyl-1H-1,2,4-triazole-5-carboxamide (5b)

A mixture of N-(3-bromo-2-(2-(difluoromethyl)phenyl)-1-((2-(trimethylsilyl)ethoxy) methyl)-1H-pyrrolo[3,2-c]pyridin-6-yl)-1-methyl-1H-1,2,4-triazole-5-carboxamide (5a) (300 mg, 0.52 mmol), zinc cyanide (183 mg, 1.56 mmol) and Pd(PPh$_3$)$_4$ (300 mg, 0.26 mmol) in DMF (10 mL) was stirred under argon atmosphere at 125° C. for 4 h. The mixture was cooled to rt and then poured into water (100 mL). The mixture was extracted with DCM (2×300 mL). The combined organic layers were dried over anhydrous $Na_2SO_4$, filtered and concentrated to dryness. The residue was purified by silica gel column chromatography (PE/EtOAc=4:1) to give the title compound as a yellow solid.

Step 3: N-(3-Cyano-2-(2-(difluoromethyl)phenyl)-1H-pyrrolo[3,2-c]pyridin-6-yl)-1-methyl-1H-1,2,4-triazole-5-carboxamide To a solution of N-(3-cyano-2-(2-(difluoromethyl)phenyl)-1-((2-(trimethylsilyl) ethoxy)methyl)-1H-pyrrolo[3,2-c]pyridin-6-yl)-1-methyl-1H-1,2,4-triazole-5-carboxamide (5b) (220 mg, 0.42 mmol) in DCM (5 mL) was added BF$_3$.Et$_2$O (1 mL) and the mixture was stirred at rt for 2 h. The mixture was diluted with water (1 mL) and concentrated. The residue was dissolved in MeOH (10 mL) and the pH was adjusted to pH=11 using 10% aqueous KOH solution. The mixture was stirred at rt for 2 h. Water was added (30 ml) and the mixture was extracted with EtOAc (3×20 mL). The combined organic layers were dried over anhydrous $Na_2SO_4$, filtered and concentrated to dryness. The residue was purified by silica gel chromatography (DCM/MeOH=10:1) to give the title compound as a white solid. $^1$H NMR (DMSO-d$_6$, 400 MHz): δ ppm 12.96 (s, 1H), 10.23 (s, 1H), 8.84 (s, 1H), 8.32 (s, 1H), 8.19 (s, 1H), 7.90-7.88 (m, 1H), 7.82-7.79 (m, 2H), 7.75-7.72 (m, 1H), 7.04 (t, J=54.4 Hz, 1H), 4.22 (s, 3H). (ESI): m/z [M+H]$^+$.

Biological Assays

AhR direct luciferase reporter assay in HepG2 cells.

A stable cell line (HepG2 CYP1A1-LUC) was used in which part of the promoter region of the human CYP1A1 gene is stably integrated into the genome of human HepG2 hepatocytes (DSZM #ACC 180) in front of a *Photinus pyralis* Firefly Luciferase gene. A 1210 bp fragment comprising part of the human CYP1A1 promoter was isolated via SacI and BglII restriction digestion from Lightswitch Clone S714555 (SwitchGearGenomics) and inserted between the SacI and BglII sites in pGL4.30 (Promega #E8481) in front of the Firefly Luciferase gene. The resulting vector was linearized with NotI, transfected into HepG2 cells (DSMZ #ACC 180) and stably transfected clones selected with 250 μg/ml Hygromycin B. After repetitive rounds of subcloning and testing for robustly regulated luciferase activity after AhR agonist stimulation, a stable clonal HepG2 CYP1A1-Luc cell line was selected.

The HepG2 CYP1A1-Luc cells do express basal luciferase activity that can be increased via potent AhR agonists or decreased via potent AhR antagonists, added to the growth medium of the cells.

In typical reporter assays performed with this cell line, cells are grown in 96-well plates and AhR modulators are titrated into the growth medium in serial dilutions in RPMI-1640 Medium (Sigma #R7509) supplemented with 8.6% fetal calf serum (Sigma #F7524) and containing either no exogenous AhR agonist or 10 nM of the potent AhR agonist VAF347 (Calbiochem #182690). Cells are further cultivated for 18 hours and luciferase activities are determined from extracts of cells in buffers containing D-Luciferine and ATP using a LUMIstar Optima microplate Luminometer from BMG Labtech.

The AhR antagonistic potency of the example compounds is shown in Table 1 below (A=IC$_{50}$<100 nM, B=IC$_{50}$ 100 nM-1 μM, C=IC$_{50}$>1 μM)

TABLE 1

| Example # | AhR potency |
| --- | --- |
| 1 | B |
| 1/1 | A |
| 1/2 | A |
| 1/3 | A |
| 1/4 | A |
| 1/5 | C |
| 1/6 | A |
| 1/7 | A |
| 1/8 | A |
| 1/9 | B |
| 1/10 | A |
| 1/11 | A |
| 1/12 | B |
| 1/13 | A |
| 2 | B |
| 2/1 | A |
| 2/2 | B |
| 2/3 | A |
| 2/4 | A |
| 2/5 | B |
| 2/6 | A |
| 2/7 | C |
| 3 | B |
| 4 | A |
| 4/1 | B |
| 4/2 | A |
| 4/3 | A |
| 5 | B |

The invention claimed is:

1. A compound represented by Formula (I), an enantiomer, diastereomer, tautomer, or pharmaceutical acceptable salt thereof

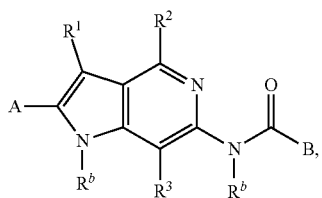

wherein
A is

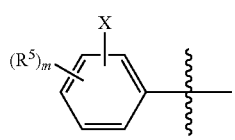

wherein
X is halogen, $C_{1-6}$-alkyl, halo-$C_{1-6}$-alkyl, or cyclopropyl,
wherein the alkyl and cycloalkyl are unsubstituted or substituted with 1 to 3 substituents independently selected from the group consisting of halogen, $C_{1-3}$-alkyl, and halo-$C_{1-3}$-alkyl;
$R^5$ is independently halogen or CN; and
m is 0 to 4;
B is

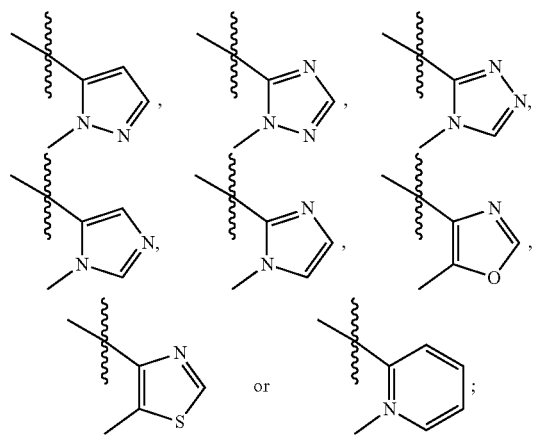

$R^1$, $R^2$, $R^3$ are each independently selected from hydrogen, halogen, $C_{1-3}$-alkyl, halo-$C_{1-3}$-alkyl, OH, O—$C_{1-3}$-alkyl, and CN;
and
$R^b$ is hydrogen or $C_{1-6}$-alkyl.

2. The compound of claim 1, wherein $R^b$ is hydrogen.
3. The compound of claim 1, wherein
A is

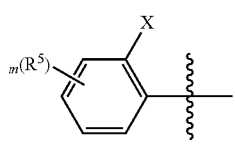

wherein
X is $CH_3$, $CHF_2$ or $CF_3$;
$R^5$ is independently halogen or CN; and
m is 0 to 4.

4. The compound of claim 1, wherein each of $R^1$, $R^2$, $R^3$ are hydrogen.

5. The compound of claim 1, wherein the compound is selected from

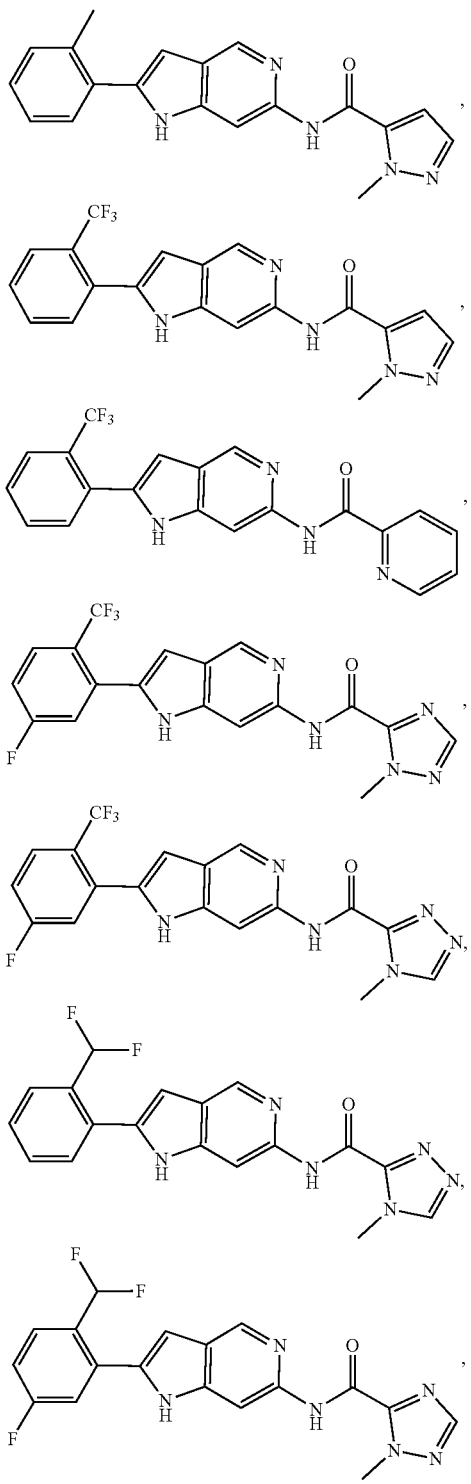

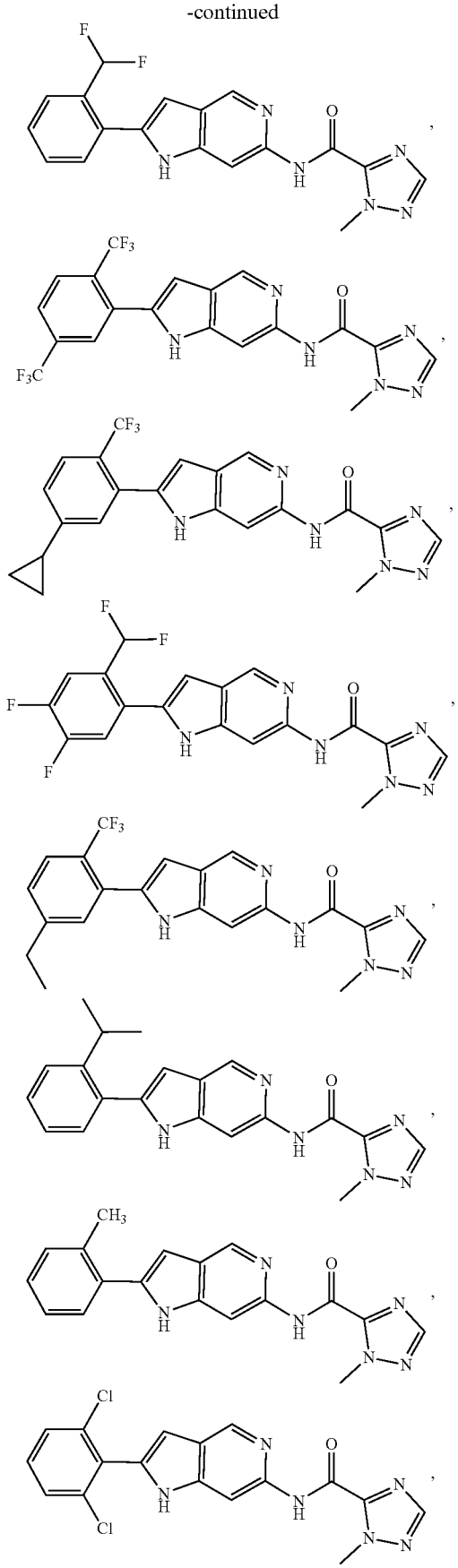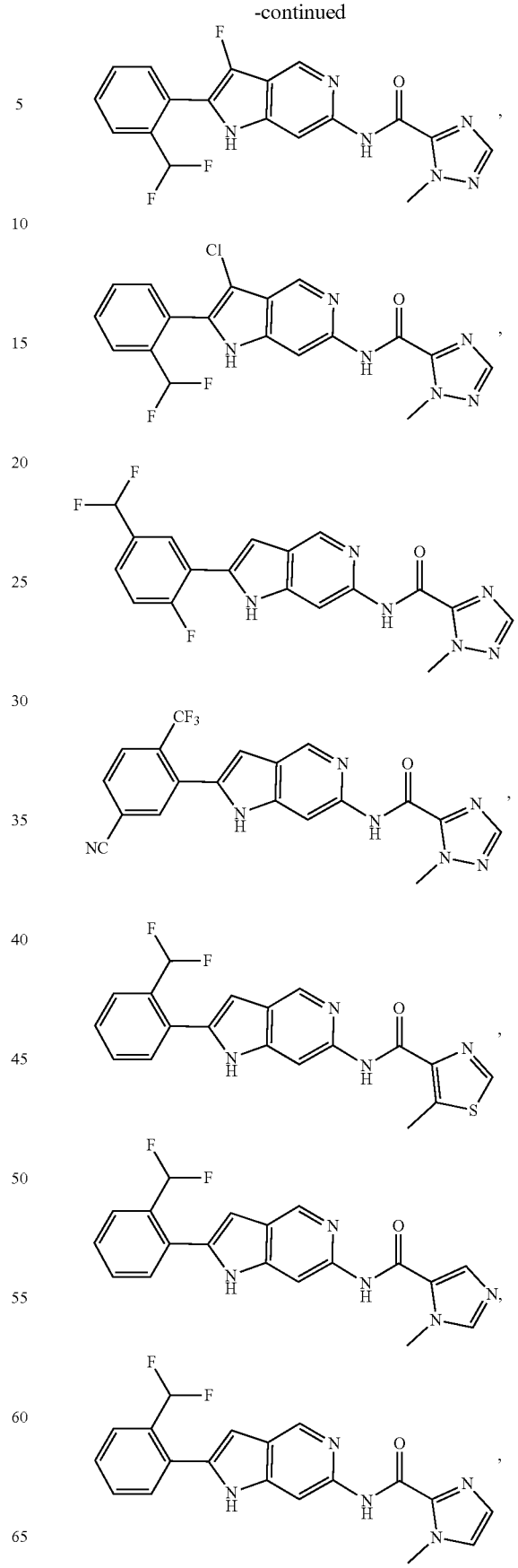

63

-continued

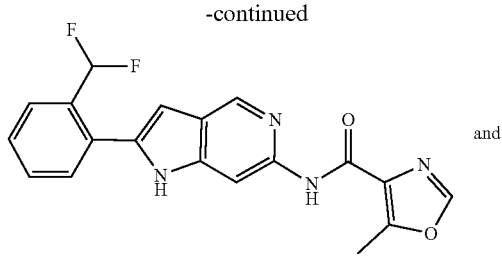

and

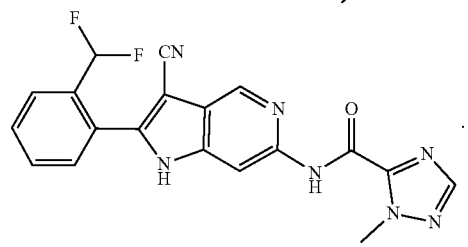

6. A pharmaceutical composition comprising the compound of claim 1 and a physiologically acceptable excipient.

7. A method for treating a disease or condition, the method comprising administering the compound of claim 1 to a subject, wherein the disease or condition is mediated by aryl hydrocarbon receptor (AhR), wherein the disease or condition mediated by aryl hydrocarbon receptor (AhR) is cancer.

8. The method of claim 7, wherein the compound is administered with one or more therapeutic agents for cancer selected from the group consisting of PD-1 agent, PD-L1 agent, CTLA-4 agent, IDO1 inhibitor, chemotherapeutic agent, anticancer vaccine, and cytokine therapy, or wherein the compound is administered under irradiation therapy.

9. A method for treating a disease or condition, the method comprising administering the pharmaceutical composition of claim 6 to a subject, wherein the disease or condition is mediated by aryl hydrocarbon receptor (AhR) wherein the disease or condition mediated by aryl hydrocarbon receptor (AhR) is cancer.

10. A compound selected from the group consisting of

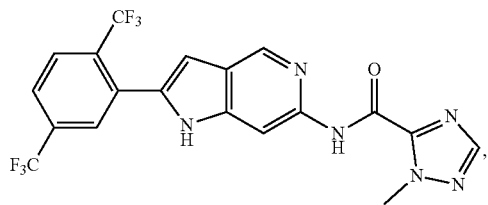

64

-continued

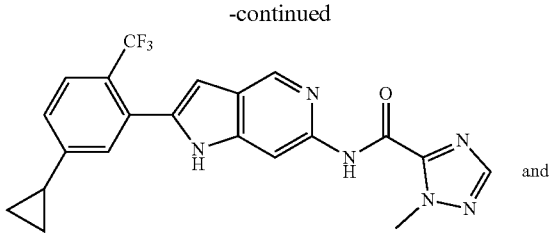

and

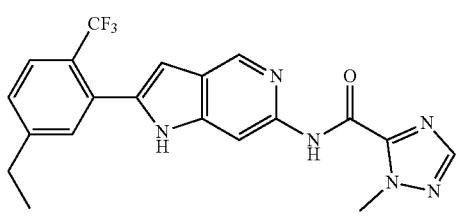

tautomer, or pharmaceutical acceptable salt thereof.

11. A pharmaceutical composition comprising the compound of claim 10 and a physiologically acceptable excipient.

12. A method for treating a disease or condition, the method comprising administering the compound of claim 10 to a subject, wherein the disease or condition is mediated by aryl hydrocarbon receptor (AhR), wherein the disease or condition mediated by aryl hydrocarbon receptor (AhR) is cancer.

13. The method of claim 12, wherein the compound is administered with one or more therapeutic agents for cancer selected from the group consisting of PD-1 agent, PD-L1 agent, CTLA-4 agent, IDO1 inhibitor, chemotherapeutic agent, anticancer vaccine, and cytokine therapy, or wherein the compound is administered under irradiation therapy.

14. A method for treating a disease or condition, the method comprising administering the pharmaceutical composition of claim 11 to a subject, wherein the disease or condition is mediated by aryl hydrocarbon receptor (AhR) wherein the disease or condition mediated by aryl hydrocarbon receptor (AhR) is cancer.

* * * * *